US010039789B2

(12) United States Patent
Stephenne et al.

(10) Patent No.: US 10,039,789 B2
(45) Date of Patent: Aug. 7, 2018

(54) COMPOSITIONS AND METHODS FOR CELL TRANSPLANTATION

(71) Applicant: UNIVERSITÉ CATHOLIQUE DE LOUVAIN, Louvain-la-Neuve (BE)

(72) Inventors: Xavier Stephenne, Rixensart (BE); Etienne Sokal, Hoeilaart (BE); Mustapha Najimi, Brussels (BE); Stéphane Eeckhoudt, Erbisoeul (BE); Cédric Hermans, Brussels (BE)

(73) Assignee: UNIVERSITÉ CATHOLIQUE DE LOUVAIN, Louvain-la-Neuve (BE)

( * ) Notice: Subject to any disclaimer, the term of this patent is extended or adjusted under 35 U.S.C. 154(b) by 0 days.

(21) Appl. No.: 15/287,061

(22) Filed: Oct. 6, 2016

(65) Prior Publication Data
US 2017/0042940 A1 Feb. 16, 2017

Related U.S. Application Data

(62) Division of application No. 13/981,720, filed as application No. PCT/EP2012/051157 on Jan. 25, 2012.

(30) Foreign Application Priority Data

Jan. 25, 2011 (EP) .................................. 11152119

(51) Int. Cl.
A61K 35/28 (2015.01)
A61K 31/727 (2006.01)
A61K 35/407 (2015.01)
A61K 38/58 (2006.01)
A61K 45/06 (2006.01)
A61K 31/737 (2006.01)
A61K 38/55 (2006.01)

(52) U.S. Cl.
CPC ............ *A61K 35/28* (2013.01); *A61K 31/727* (2013.01); *A61K 31/737* (2013.01); *A61K 35/407* (2013.01); *A61K 38/55* (2013.01); *A61K 38/58* (2013.01); *A61K 45/06* (2013.01)

(58) Field of Classification Search
None
See application file for complete search history.

(56) References Cited

U.S. PATENT DOCUMENTS

2005/0118274 A1 6/2005 Bader
2013/0302291 A1 11/2013 Stephenne et al.
2015/0037291 A1 2/2015 Stephenne et al.

FOREIGN PATENT DOCUMENTS

JP 2009-508650 A 3/2009
JP 2009-520474 A 5/2009
WO WO 01/95931 A1 12/2001
WO WO 2006/103206 A2 10/2006
WO WO 2007/035843 A2 3/2007
WO WO 2007/071339 A1 6/2007

OTHER PUBLICATIONS

Gupta, S., Wilson, J. M., & Roy Chowdhury, J. (1992). Hepatocyte transplantation: Development of new systems for liver repopulation and gene therapy. Seminars in Liver Disease, 12(3), 321-331. (Year: 1992).*
International Search Report for International Application No. PCT/EP2012/051157, dated May 7, 2012, in 6 pages.
Akima et al., "Tirofiban and Activated Protein C Synergistically Inhibit the Instant Blood Mediated Inflammatory Reaction (IBMIR) from Allogeneic Islet Cells Exposure to Human Blood," American Journal of Transplantation, vol. 9, pp. 1533-1540 (2009).
Biemond et al., "Additive Effect of the Combined Administration of Low Molecular Weight Heparin and Recombinant Hirudin on Thrombus Growth in a Rabbit Jugular Vein Thrombosis Model," Thrombosis and Haemostasis, F. K. Schattauer Verlagsgesellschaft mbH, Stuttgart, Germany, vol. 72(3), pp. 377-380 (1994).
Brenner et al., "Prevention of hyperacute xenograft rejection through direct thrombin inhibition with hirudin," Ann Transplant, vol. 15(4), pp. 30-37 (2010).
Chen et al., "Low dose heparin for the prevention of hepatic veno-occlusive disease after allogeneic hematopoietic stem cell transplantation," Chinese Journal of Internal Medicine, vol. 46(2), pp. 140-142 (Feb. 2007).
Cuccuini et al., "Tissue factor up-regulation in proinflammatory conditions confers thrombin generation capacity to endothelial colony-forming cells without influencing non-coagulant properties in vitro," Journal of Thrombosis and Haemostasis, vol. 8, pp. 2042-2052 (2010).
Giardino et al., "Cooperative antithrombotic effect from the simultaneous inhibition of thrombin and factor Xa," Blood Coagulation and Fibrinolysis, vol. 21, pp. 128-134 (2010).
Gleeson et al., "Bone Marrow-Derived Mesenchymal Stem Cells Have Innate Procoagulant Activity and Cause Microvascular Obstruction Following Intracoronary Delivery: Amelioration by Antithrombin Therapy," Stem Cells, vol. 33, pp. 2726-2737 (2015).
Linder et al., "The influence of direct and antithrombin-dependent thrombin inhibitors on the procoagulant and anticoagulant effects of thrombin," Thrombosis Research, vol. 110, pp. 221-226 (2003).
Lisman et al. "Rebalanced hemostasis in patients with liver disease: evidence and clinical consequences" Blood Aug. 12, 2010. vol. 116(6). pp. 878-885.
Lisman et al. J Hepatology (2010) vol. 52: pp. 355-361.

(Continued)

Primary Examiner — Leon B Lankford, Jr.
(74) Attorney, Agent, or Firm — Knobbe Martens Olson & Bear LLP

(57) ABSTRACT

The present invention relates to compositions and methods for cell transplantation. In particular, the present invention provides a composition comprising procoagulant cells and at least one antithrombin activator, preferably unfractionated heparin, as well as at least one thrombin inhibitor, preferably bivalirudin.

13 Claims, 23 Drawing Sheets

(56) References Cited

OTHER PUBLICATIONS

Moll et al., "Different Procoagulant Activity of Therapeutic Mesenchymal Stromal Cells Derived from Bone Marrow and Placental Decidua," Stem Cells and Development, vol. 24(19), pp. 2269-2279 (2015).
Smets et al., "Cell transplantation in the treatment of liver diseases," Pediatric Transplantation, vol. 12, pp. 6-13 (2008).
Stephenne et al., "Bivalirudin in Combination with Heparin to Control Mesenchymal Cell Procoagulant Activity," PLOS ONE, vol. 7(8), p. e42819 (Aug. 2012).
Stephenne et al., Supplemental Figures S1-S10 for "Bivalirudin in Combination with Heparin to Control Mesenchymal Cell Procoagulant Activity," PLOS ONE, vol. 7(8), p. e42819 (Aug. 2012).
Tsakiris et al., "Thrombotic complications after haematopoietic stem cell transplantation: early and late effects," Best Practice & Research Clinical Haematology, vol. 22, pp. 137-145 (2009).
Welsby et al., "Effect of Combined Anticoagulation Using Heparin and Bivalirudin on the Hemostatic and Inflammatory Responses to Cardiopulmonary Bypass in the Rat," Anesthesiology, vol. 106(2), pp. 295-301 (Feb. 2007).

\* cited by examiner

FIG 1
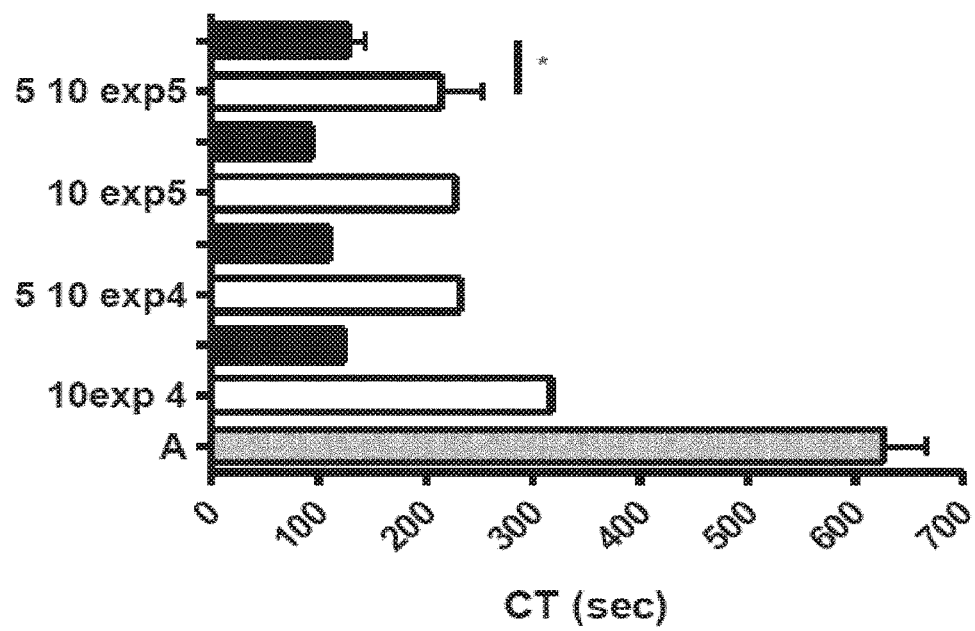
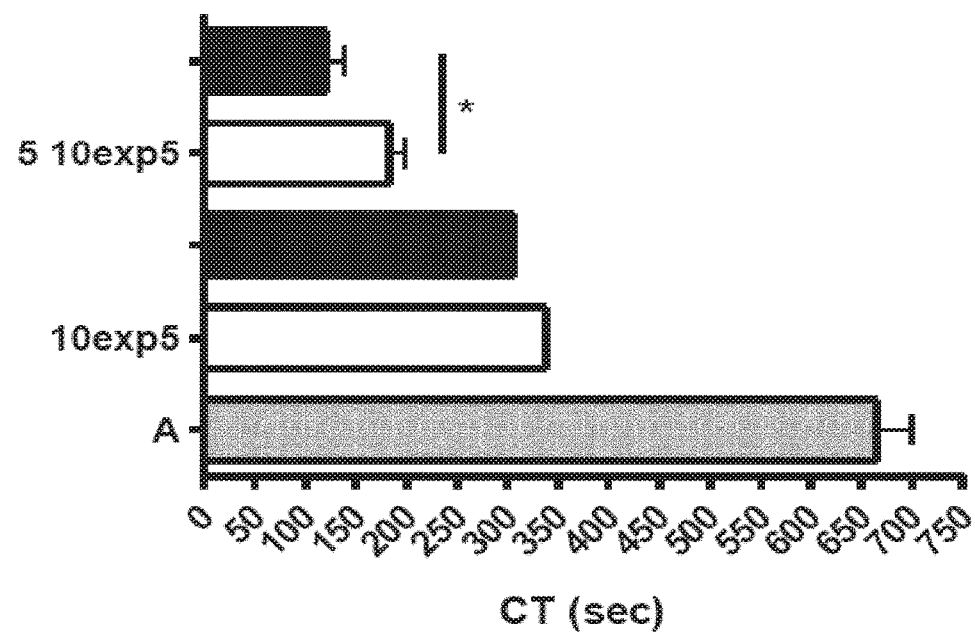

FIG 7
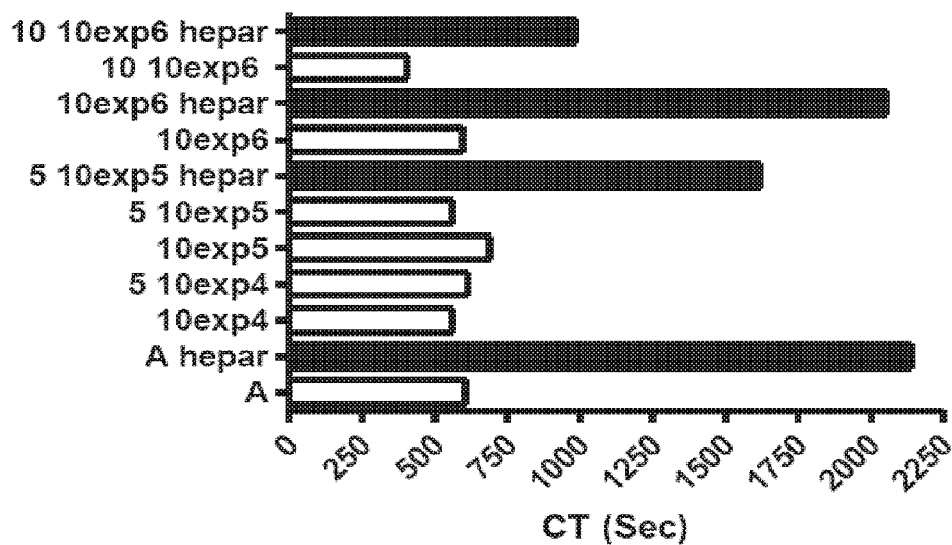
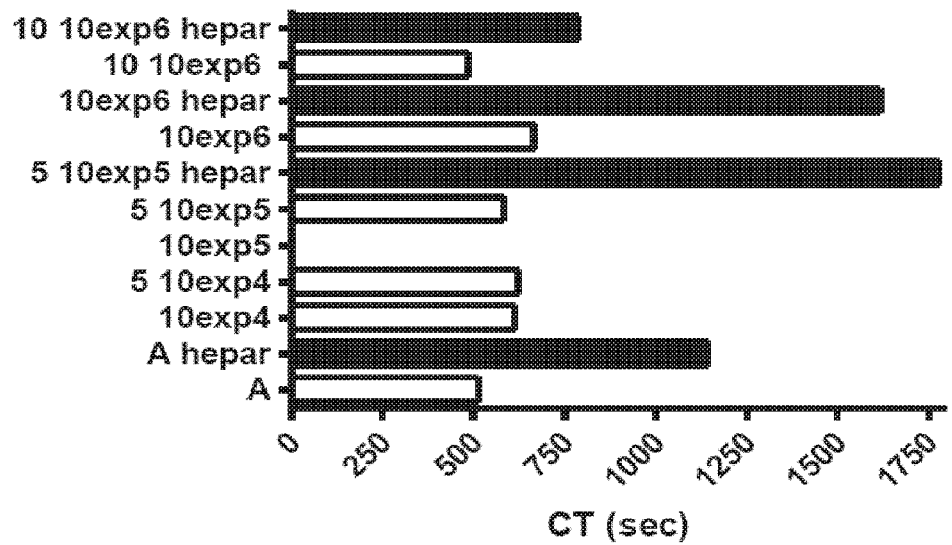

FIG 10
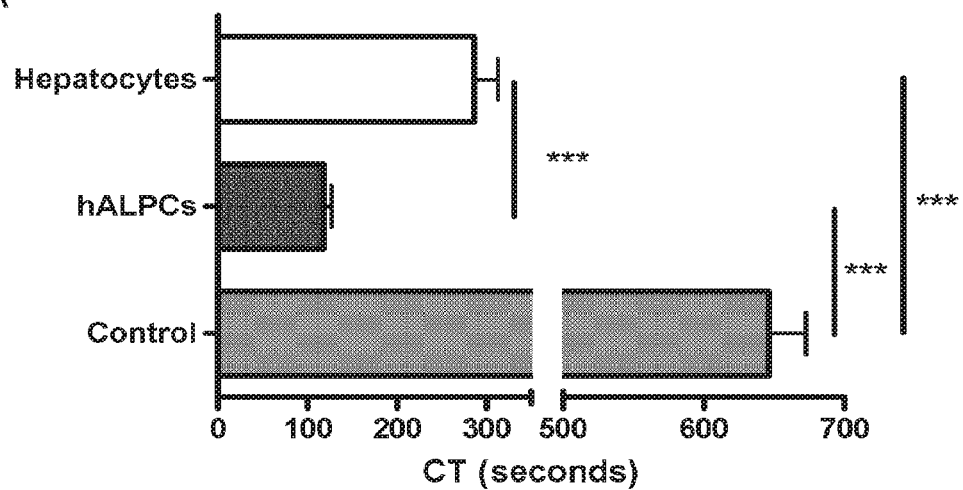
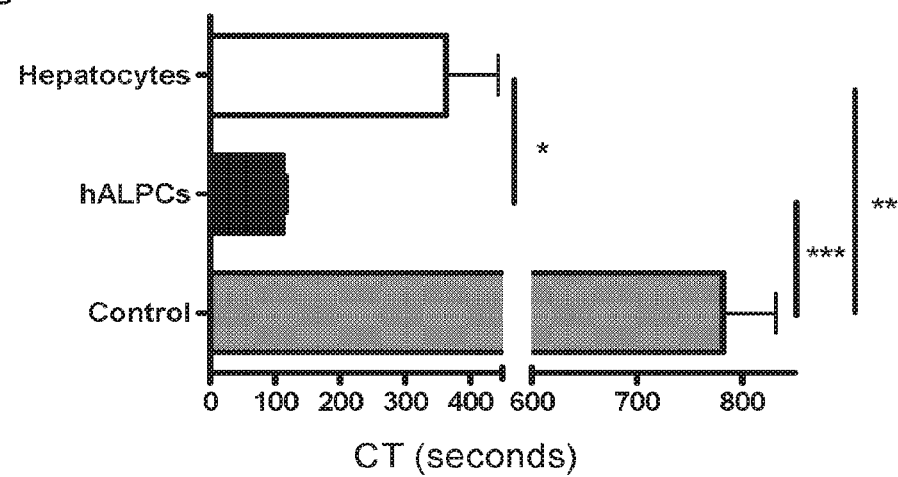

Figure 15:
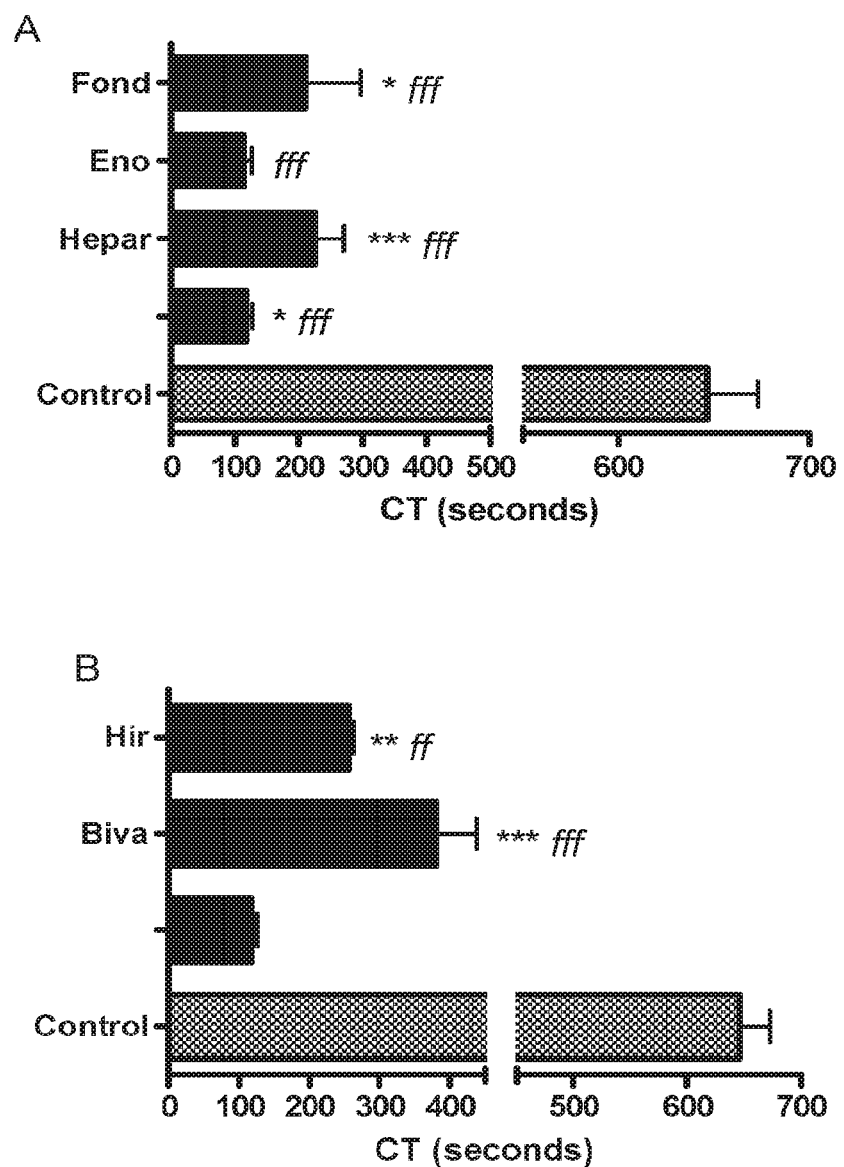

FIG 15
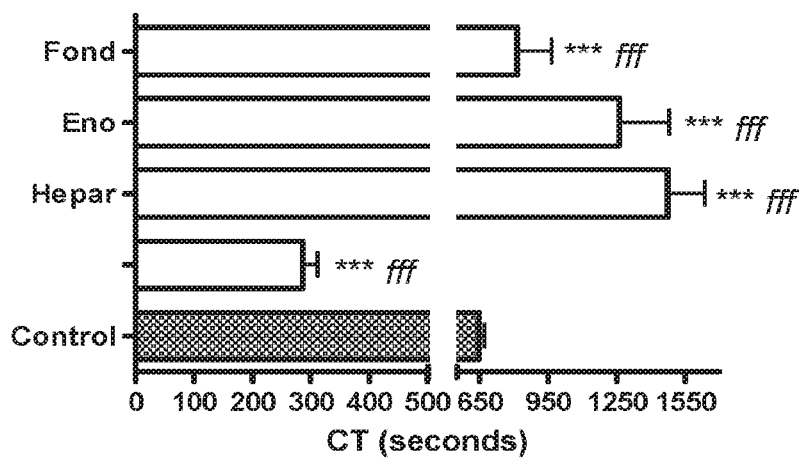
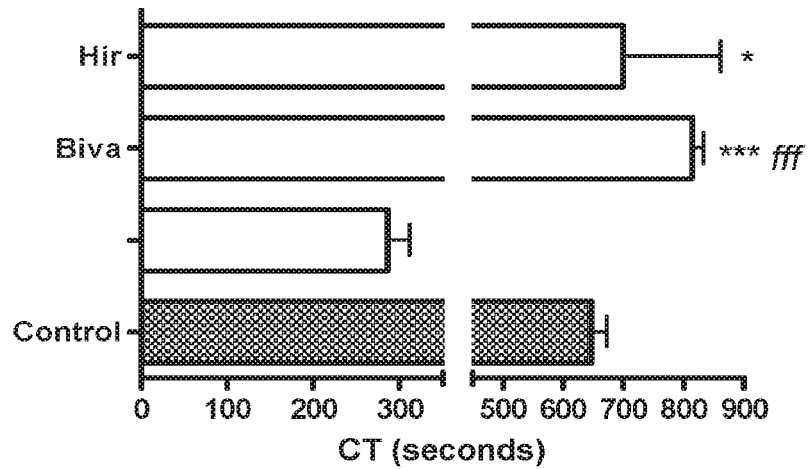

FIG 16
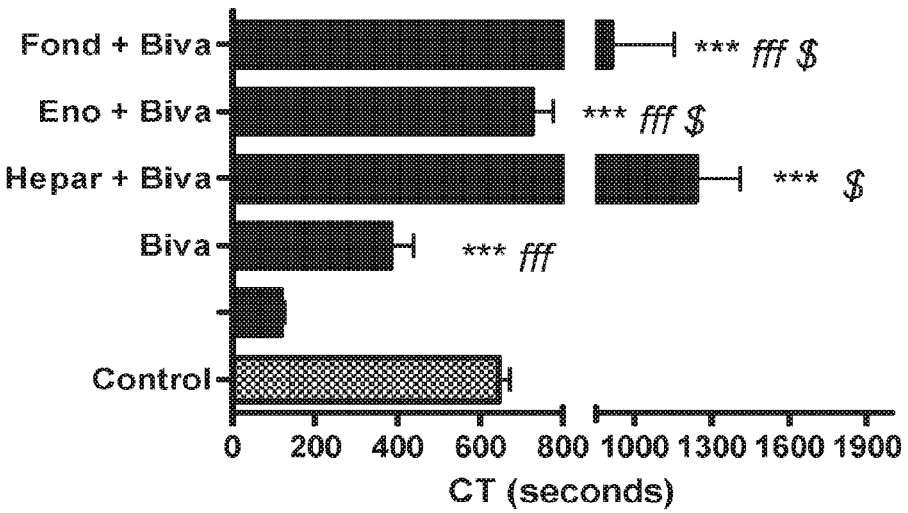
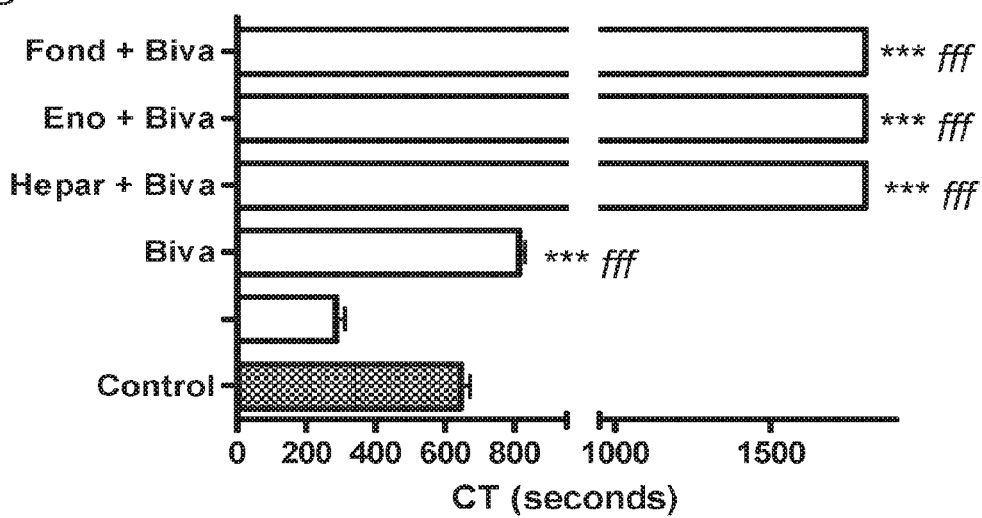

FIG 23
A)
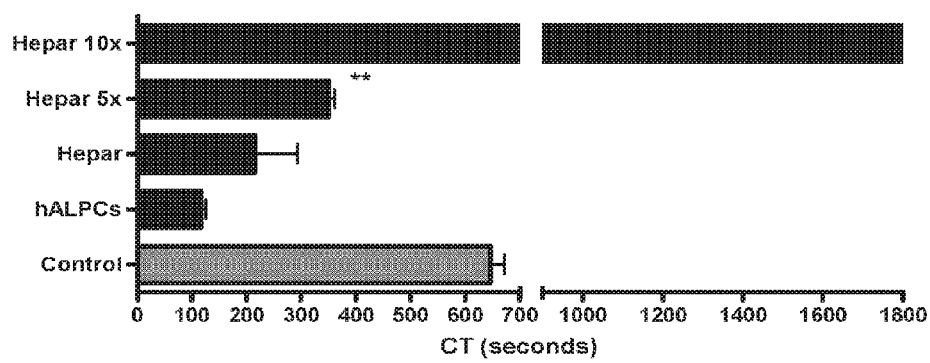
B)
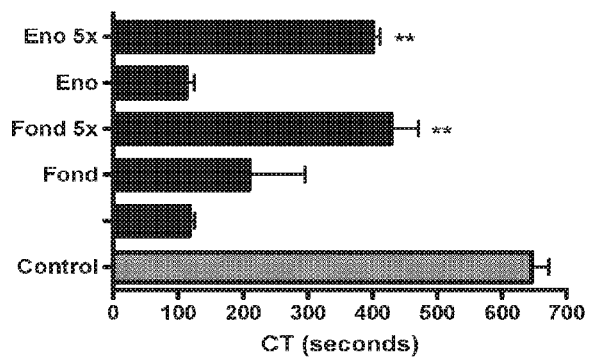

SEQUENCE LISTING

<160> NUMBER OF SEQ ID NOS: 8

<210> SEQ ID NO 1
<211> LENGTH: 22
<212> TYPE: DNA
<213> ORGANISM: Artificial
<220> FEATURE:
<223> OTHER INFORMATION: Primer

<400> SEQUENCE: 1
tgaatgtgac cgtagaagat ga                                                 22

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
ggagttctcc ttccagctct                                                    20

<210> SEQ ID NO 3
<211> LENGTH: 25
<212> TYPE: DNA
<213> ORGANISM: Artificial
<220> FEATURE:
<223> OTHER INFORMATION: Primer

<400> SEQUENCE: 3
ggaagaagat cctggaatat cgagg                                              25

<210> SEQ ID NO 4
<211> LENGTH: 25
<212> TYPE: DNA
<213> ORGANISM: Artificial
<220> FEATURE:
<223> OTHER INFORMATION: Primer

<400> SEQUENCE: 4
cttggttgat tgcggagtca gggag                                              25

<210> SEQ ID NO 5
<211> LENGTH: 24
<212> TYPE: DNA
<213> ORGANISM: Artificial
<220> FEATURE:
<223> OTHER INFORMATION: Primer

<400> SEQUENCE: 5
cggactcaac ggatttggtc gtat                                               24

<210> SEQ ID NO 6
<211> LENGTH: 18
<212> TYPE: DNA
<213> ORGANISM: Artificial
<220> FEATURE:
<223> OTHER INFORMATION: Primer

<400> SEQUENCE: 6
agccttctcc atggtggt                                                      18

<210> SEQ ID NO 7
<211> LENGTH: 27
<212> TYPE: DNA
<213> ORGANISM: Artificial

```
<220> FEATURE:
<223> OTHER INFORMATION: Primer

<400> SEQUENCE: 7
tcttcaagtt caggaaagaa atattct                                              27

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
ccaggatgat gacaaggatg a                                                    21
```

COMPOSITIONS AND METHODS FOR CELL TRANSPLANTATION

CROSS-REFERENCE TO RELATED APPLICATIONS

This application is a divisional of U.S. application Ser. No. 13/981,720, filed Jul. 25, 2013 which is the U.S. National Phase under 35 U.S.C. § 371 of International Application PCT/EP2012/051157, filed Jan. 25, 2012, which claims priority to EP 11152119.1, filed Jan. 25, 2011.

FIELD OF THE INVENTION

The present invention relates to the field of tissue regeneration in general and cell transplantation in particular. The present invention is directed at compositions and methods for improving cell transplantation and particularly for inhibiting procoagulant activity associated with cell transplantation.

BACKGROUND OF THE INVENTION

Various conditions caused by diseased or otherwise damaged or functionally impaired organs may be treated by organ transplantations. In particular, transplantation of heart, kidneys, liver, lungs, pancreas, intestine, and thymus can routinely be performed with a reasonable rate of success. A major drawback in organ transplantation however remains the need to find a compatible donor for each recipient patient, since incompatibility between the donor and recipient may result in rejection of the transplanted organ. Transplant rejection can be reduced through serotyping to determine the most appropriate donor-recipient match and through the use of immunosuppressant drugs, although the suitability of these approaches may be diminished due to the medical urgency in some cases. Also, life-long use of immunosuppressant drugs places a burden on the recipient patient in terms of side effects and compliance.

In recent years, cell therapy using various sources of cells is increasingly used for regenerative medicine in humans. Transplantation of cells may provide a valuable alternative or additional (adjunctive) therapy to organ transplantations. Moreover, as not all organs can be effectively transplanted, cell transplantation may frequently be the only cure available. Advantageously, in cell transplantation compatibility related complications may at least in theory become less of a problem. For example, the cells to be transplanted can sometimes be isolated or derived from the patient himself (i.e. autologous cell transplantation), thereby reducing the risk of rejection. Alternatively, allogeneic or even xenogeneic transplant cells may be readily typed and stored for a prolonged time in cell banks or inventories, from which genetically matching or at least compatible cells may be obtained for most recipients.

Where administration of cells to a patient is contemplated, it may be preferable that the cells or cell cultures are selected such as to maximise the tissue compatibility between the patient and the administered cells, thereby reducing the chance of rejection of the administered cells by patient's immune system (graft vs. host rejection). For example, advantageously the cells may be typically selected which have either identical HLA haplotypes (including one or preferably more HLA-A, HLA-B, HLA-C, HLA-D, HLA-DR, HLA-DP and HLA-DQ; preferably one or preferably all HLA-A, HLA-B and HLA-C) to the patient, or which have the most HLA antigen alleles common to the patient and none or the least of HLA antigens to which the patient contains pre-existing anti-HLA antibodies.

Tissue regeneration procedures by means of cell transplantation may be executed using a large variety of cell sources, and commonly using cells having proliferative capacity. For instance, in various human inborn metabolic diseases liver cell transplantation can restore at least some degree of metabolic control. In another example, intraportal transplantation of pancreatic islets offers improved glycaemic control and insulin independence in type 1 diabetes mellitus. For example, pluripotent stem cells capable of differentiating into a plethora of cell lineages, or progenitor cells committed to one or a few cell lineages (multipotent) and displaying varying degrees of differentiation may be used as a cell source for cell transplantation.

Despite some clinical success, current cell transplantation therapies are in need of further improvements. One concern among clinicians and health authorities are the potential consequences of procoagulant activity of certain transplanted cells on engraftment of the cells and other complications. For example, procoagulant activity of islet transplants has been reported to cause graft loss and intraportal thrombotic events (Beuneu et al. Diabetes, 2004, vol. 53, 1407-11; Moberg et al. Lancet, 2002, vol. 360, 2039-45). Procoagulant activity has been also observed in isolated primary hepatocytes (Stéphenne et al. Liver Transpl., 2007, vol. 13, 599-606).

Consequently, there persists an urgent need in the art to improve cell transplantation success and cell engraftment potential, and in particular to reduce prothrombotic complications associated with cell transplantation.

Furlani et al. Microvasc Res., 2009, vol. 77, 370-6 studied the kinetics of human mesenchymal stem cells after intravascular administration into SCID mouse cremaster vasculature by intra-vital microscopy. The authors proposed that intra-arterial mesenchymal stem cells infusion may lead to occlusion in the distal vasculature due to the cells' relatively large size.

SUMMARY OF THE INVENTION

Having conducted extensive in vitro and clinical evaluations the inventors have learned that procoagulant activity previously reported for isolated primary cells such as hepatocytes and islet cells is also observed for stem cells and progenitor cells such as mesenchymal stem cells. The procoagulant activity of stem and progenitor cells may be of concern for transplantation of these cells, in particular may cause undesired bloodstream modifications, loss of the transplanted cells, reduction of the cell engraftment potential and/or thrombotic events. Moreover, this procoagulant activity cannot be controlled by unfractionated heparin, the conventional anticoagulant for hepatocyte transplantation.

The inventors therefore investigated manners to counteract the procoagulant activity of transplanted cells and found that concomitant or associated administration of cells having procoagulant activity with an antithrombin activator and a thrombin inhibitor provides a particularly effective and safe combination for preventing deleterious procoagulant effects. Surprisingly, whereas concomitant administration of cells having procoagulant activity with either one of an antithrombin activator or a thrombin inhibitor alone does not adequately prevent thrombotic events at physiologically acceptable concentrations of respectively the antithrombin activator or thrombin inhibitor, the combination of the antithrombin activator together with the thrombin inhibitor can advantageously prevent cell therapy-induced thrombosis and thrombosis associated complications (e.g., local thrombosis and induction of local inflammation). Accordingly, the inventors realised a particularly advantageous and even synergistic combination therapy and clinical protocols useful for reducing procoagulant activity of transplanted cells, in particular stem and progenitor cells.

Accordingly, an aspect relates to a combination comprising cells having procoagulant activity, at least one antithrombin activator, and at least one thrombin inhibitor.

Another aspect relates to a combination comprising at least one antithrombin activator, at least one thrombin inhibitor, and cells selected from the group comprising or consisting of adult liver progenitor cells, mesenchymal stem cells (preferably bone marrow mesenchymal stem cells), skin fibroblasts, and liver myofibroblasts, more preferably selected from adult liver progenitor cells and liver myofibroblasts.

Where applicable, the combination may be configured for separate, simultaneous or sequential in any order administration of the cells, at least one antithrombin activator, and at least one thrombin inhibitor. Moreover, the cells, at least one antithrombin activator, and/or at least one thrombin inhibitor in said combination may be admixed or may be separate. Also disclosed is a method for producing said combination comprising combining the cells, at least one antithrombin activator, and at least one thrombin inhibitor.

As intended throughout this specification when referring to a combination comprising cells as described herein such as particularly to cells having procoagulant activity, at least one antithrombin activator, and at least one thrombin inhibitor, or when referring to a combination comprising at least one antithrombin activator and at least one thrombin inhibitor, or when referring to any subject matter comprising or employing such a combination, the individual constituents of the combination may be configured for separate, simultaneous or sequential in any order administration to a subject, or may be administered to a subject separately, simultaneously or sequentially in any order. In an example, the cells, the at least one antithrombin activator and the at least one thrombin inhibitor may all be included in the cell suspension to be administered. In another example, the cells and the at least one antithrombin activator may be included in the cell suspension to be administered, whereas the at least one thrombin inhibitor may be held separate from said cell suspension and to be administered to the subject simultaneously or sequentially with said cell suspension. In yet another example, the cells and the at least one thrombin inhibitor may be included in the cell suspension to be administered, whereas the at least one antithrombin activator may be held separate from said cell suspension and to be administered to the subject simultaneously or sequentially with said cell suspension. In a further example, both the at least one antithrombin activator and the at least one thrombin inhibitor may be held separate from the cell suspension and to be administered to the subject simultaneously or sequentially with the cell suspension, and simultaneously or sequentially with one another. Where administration of the constituents is sequential, it shall be understood that the timing of administration shall be chosen to allow for the desired actions of the constituents brought about by their combination.

Further disclosed is a pharmaceutical composition comprising (a) a combination comprising cells having procoagulant activity, at least one antithrombin activator, at least one thrombin inhibitor and (b) one or more pharmaceutically acceptable excipients.

Further disclosed is a pharmaceutical composition comprising (a) a combination comprising at least one antithrombin activator, at least one thrombin inhibitor, and cells selected from the group comprising or consisting of adult liver progenitor cells, mesenchymal stem cells (preferably bone marrow mesenchymal stem cells), skin fibroblasts, and liver myofibroblasts, more preferably selected from adult liver progenitor cells and liver myofibroblasts, and (b) one or more pharmaceutically acceptable excipients.

The pharmaceutical composition may be configured for separate, simultaneous or sequential in any order administration of the cells, at least one antithrombin activator, and at least one thrombin inhibitor. The cells, at least one antithrombin activator, and/or at least one thrombin inhibitor in said pharmaceutical composition may be admixed or may be separate. Also disclosed is a method for producing said pharmaceutical composition comprising admixing the cells, at least one antithrombin activator, and at least one thrombin inhibitor, each separately or in an admixture, with the one or more pharmaceutically acceptable excipients.

As well provided is a kit of parts or an article of manufacture comprising a combination comprising cells having procoagulant activity, at least one antithrombin activator, and at least one thrombin inhibitor, and optionally further comprising one or more pharmaceutically acceptable excipients.

As well provided is a kit of parts or an article of manufacture comprising a combination comprising at least one antithrombin activator, at least one thrombin inhibitor, and cells selected from the group comprising or consisting of adult liver progenitor cells, mesenchymal stem cells (preferably bone marrow mesenchymal stem cells), skin fibroblasts, and liver myofibroblasts, more preferably selected from adult liver progenitor cells and liver myofibroblasts, and optionally further comprising one or more pharmaceutically acceptable excipients.

The kit of parts or article of manufacture may be configured for separate, simultaneous or sequential in any order administration of the cells, at least one antithrombin activator, and at least one thrombin inhibitor. The cells, at least one antithrombin activator, and/or at least one thrombin inhibitor in said kit of parts or article of manufacture may be admixed or may be separate, particularly may be separate such as for example contained in separate containers. Also disclosed is a method for producing said kit of parts or article of manufacture comprising including the cells, at least one antithrombin activator, and at least one thrombin inhibitor, and optionally one or more pharmaceutically acceptable excipients, in a kit of parts or an article of manufacture. Also provided is the kit of parts or article of manufacture for use in any one and each of the herein-described indications.

Further disclosed are any one and each of the following aspects:
  a combination comprising cells having procoagulant activity, at least one antithrombin activator, and at least one thrombin inhibitor for use as a medicament;
  a combination comprising at least one antithrombin activator, at least one thrombin inhibitor, and cells selected from the group comprising or consisting of adult liver progenitor cells, mesenchymal stem cells (preferably bone marrow mesenchymal stem cells), skin fibroblasts, and liver myofibroblasts, more preferably selected from adult liver progenitor cells and liver myofibroblasts, for use as a medicament;
  a combination comprising any cells as described herein such as particularly cells having procoagulant activity, at least one antithrombin activator, and at least one thrombin inhibitor, or a pharmaceutical composition comprising said combination and one or more pharmaceutically acceptable excipients, for use in transplantation of said cells;
use of a combination comprising any cells as described herein such as particularly cells having procoagulant activity, at least one antithrombin activator, and at least one thrombin inhibitor for the manufacture of a medicament for transplantation of said cells;
a combination comprising any cells as described herein such as particularly cells having procoagulant activity, at least one antithrombin activator, and at least one thrombin inhibitor, or a pharmaceutical composition comprising said combination and one or more pharmaceutically acceptable excipients, for use in the treatment of thrombosis or thrombotic complications, particularly thrombosis or thrombotic complications caused by transplantation of said cells;
use of a combination comprising any cells as described herein such as particularly cells having procoagulant activity, at least one antithrombin activator, and at least one thrombin inhibitor for the manufacture of a medicament for the treatment of thrombosis or thrombotic complications, particularly thrombosis or thrombotic complications caused by transplantation of said cells;
a combination comprising any cells as described herein such as particularly cells having procoagulant activity, at least one antithrombin activator, and at least one thrombin inhibitor, or a pharmaceutical composition comprising said combination and one or more pharmaceutically acceptable excipients, for use in inhibiting procoagulant activity of said cells in vivo;
use of a combination comprising any cells as described herein such as particularly cells having procoagulant activity, at least one antithrombin activator, and at least one thrombin inhibitor for the manufacture of a medicament for inhibiting procoagulant activity of said cells in vivo;
use of a combination comprising any cells as described herein such as particularly cells having procoagulant activity, at least one antithrombin activator, and at least one thrombin inhibitor for inhibiting the procoagulant activity of said cells in vitro;
a method for inhibiting in vitro the procoagulant activity of any cells as described herein such as particularly cells having procoagulant activity comprising providing a combination comprising said cells, at least one antithrombin activator, and at least one thrombin inhibitor;
a method for transplantation of any cells as described herein such as particularly cells having procoagulant activity to a subject in need of such transplantation comprising administering to said subject a therapeutically or prophylactically effective amount of a combination comprising said cells, at least one antithrombin activator, and at least one thrombin inhibitor, or a pharmaceutical composition comprising said combination and one or more pharmaceutically acceptable excipients;
a method for treating thrombosis or thrombotic complications, particularly thrombosis or thrombotic complications caused by transplantation of any cells as described herein such as particularly cells having procoagulant activity, in a subject in need of such treatment, comprising administering to said subject a therapeutically or prophylactically effective amount of a combination comprising said cells, at least one antithrombin activator, and at least one thrombin inhibitor, or a pharmaceutical composition comprising said combination and one or more pharmaceutically acceptable excipients;
a method for inhibiting procoagulant activity of cells, such as of any cells as described herein, in vivo in a subject in need of such inhibition, comprising administering to said subject a therapeutically or prophylactically effective amount of a combination comprising said cells, at least one antithrombin activator, and at least one thrombin inhibitor, or a pharmaceutical composition comprising said combination and one or more pharmaceutically acceptable excipients.

As well provided are uses of a combination comprising any cells as described herein such as particularly cells having procoagulant activity, at least one antithrombin activator and at least one thrombin inhibitor, in any one and each of the above-described indications.

A further aspect relates to a combination comprising at least one antithrombin activator and at least one thrombin inhibitor. Where applicable, the combination may be configured for separate, simultaneous or sequential in any order administration of the at least one antithrombin activator and at least one thrombin inhibitor. Moreover, the at least one antithrombin activator and at least one thrombin inhibitor in said combination may be admixed or may be separate. Also disclosed is a method for producing said combination comprising combining the at least one antithrombin activator and at least one thrombin inhibitor.

Further disclosed is a pharmaceutical composition comprising a combination comprising at least one antithrombin activator, at least one thrombin inhibitor and one or more pharmaceutically acceptable excipients. The pharmaceutical composition may be configured for separate, simultaneous or sequential in any order administration of the at least one antithrombin activator and at least one thrombin inhibitor. The at least one antithrombin activator and at least one thrombin inhibitor in said pharmaceutical composition may be admixed or may be separate. Also disclosed is a method for producing said pharmaceutical composition comprising admixing the at least one antithrombin activator and at least one thrombin inhibitor, each separately or in an admixture, with the one or more pharmaceutically acceptable excipients.

As well provided is a kit of parts or an article of manufacture comprising a combination comprising at least one antithrombin activator and at least one thrombin inhibitor, and optionally further comprising one or more pharmaceutically acceptable excipients. The kit of parts or article of manufacture may be configured for separate, simultaneous or sequential in any order administration of the at least one antithrombin activator and at least one thrombin inhibitor. The at least one antithrombin activator and at least one thrombin inhibitor in said kit of parts or article of manufacture may be admixed or may be separate, particularly may be separate such as for example contained in separate containers. Also disclosed is a method for producing said kit of parts or article of manufacture comprising including the at least one antithrombin activator and at least one thrombin inhibitor, and optionally one or more pharmaceutically acceptable excipients, in a kit of parts or an article of manufacture. Also provided is the kit of parts or article of manufacture for use in any one and each of the herein-described indications.

Also disclosed are any one and each of the ensuing aspects:

- a combination comprising at least one antithrombin activator and at least one thrombin inhibitor for use as a medicament;
- a combination comprising at least one antithrombin activator and at least one thrombin inhibitor, or a pharmaceutical composition comprising said combination and one or more pharmaceutically acceptable excipients, for use in transplantation of cells having procoagulant activity (i.e., in conjunction with cell transplantation);
- a combination comprising at least one antithrombin activator and at least one thrombin inhibitor, or a pharmaceutical composition comprising said combination and one or more pharmaceutically acceptable excipients, for use in transplantation of cell selected from the group comprising or consisting of adult liver progenitor cells, mesenchymal stem cells (preferably bone marrow mesenchymal stem cells), skin fibroblasts, and liver myofibroblasts, more preferably selected from adult liver progenitor cells and liver myofibroblasts (i.e., in conjunction with cell transplantation);
- use of a combination comprising at least one antithrombin activator and at least one thrombin inhibitor for the manufacture of a medicament for transplantation of any cells as described herein such as particularly cells having procoagulant activity;
- a combination comprising at least one antithrombin activator and at least one thrombin inhibitor, or a pharmaceutical composition comprising said combination and one or more pharmaceutically acceptable excipients, for use in the treatment of thrombosis or thrombotic complications, particularly thrombosis or thrombotic complications caused by transplantation of any cells as described herein such as particularly cells having procoagulant activity;
- use of a combination comprising at least one antithrombin activator and at least one thrombin inhibitor for the manufacture of a medicament for the treatment of thrombosis or thrombotic complications, particularly thrombosis or thrombotic complications caused by transplantation of any cells as described herein such as particularly cells having procoagulant activity;
- a combination comprising at least one antithrombin activator and at least one thrombin inhibitor, or a pharmaceutical composition comprising said combination and one or more pharmaceutically acceptable excipients, for use in inhibiting procoagulant activity of cells, such as of any cells as described herein, in vivo;
- use of a combination comprising at least one antithrombin activator and at least one thrombin inhibitor for the manufacture of a medicament for inhibiting procoagulant activity of cells, such as of any cells as described herein, in vivo.
- use of a combination comprising at least one antithrombin activator and at least one thrombin inhibitor for inhibiting the procoagulant activity of cells, such as of any cells as described herein, in vitro;
- a method for inhibiting in vitro the procoagulant activity of any cells as described herein such as particularly cells having procoagulant activity comprising contacting said cells with a combination comprising at least one antithrombin activator and at least one thrombin inhibitor;
- a method for treating thrombosis or thrombotic complications, particularly thrombosis or thrombotic complications caused by transplantation of any cells as described herein such as particularly cells having procoagulant activity, in a subject in need of such treatment, comprising administering to said subject a therapeutically or prophylactically effective amount of a combination comprising at least one antithrombin activator and at least one thrombin inhibitor, or a pharmaceutical composition comprising said combination and one or more pharmaceutically acceptable excipients;
- a method for inhibiting procoagulant activity of cells in vivo in a subject in need of such inhibition, comprising administering to said subject a therapeutically or prophylactically effective amount of a combination comprising at least one antithrombin activator and at least one thrombin inhibitor, or a pharmaceutical composition comprising said combination and one or more pharmaceutically acceptable excipients.

Preferably, any of the above methods may comprise the steps of: (a) preparing a composition comprising a cell suspension of the cells as described herein such as particularly cells having procoagulant activity in an aqueous solution containing the at least one antithrombin activator; (b) preparing an aqueous solution containing the at least one thrombin inhibitor (i.e., distinct from or separate from composition (a)); and (c) administering the composition as defined in (a) and the solution as defined in (b) simultaneously, separately or sequentially to the subject. Hence, preferably in the above aspects, (a) a composition comprising a cell suspension of the cells as described herein such as particularly cells having procoagulant activity in an aqueous solution containing the at least one antithrombin activator is to be prepared; (b) an aqueous solution containing the at least one thrombin inhibitor is to be prepared (i.e., distinct from or separate from composition (a)); and (c) the composition as defined in (a) and the solution as defined in (b) is to be administered simultaneously, separately or sequentially to a subject.

As well provided are uses of a combination comprising at least one antithrombin activator and at least one thrombin inhibitor in any one and each of the above-described indications.

Also provided is an arrangement comprising a surgical instrument or device for administration of a composition to a subject, such as for example systemically, topically, within an organ or tissue (e.g., portal vein of the liver, spleen, pancreas, liver, kidney capsule, peritoneum and omental pouch), and further comprising the combination or pharmaceutical composition comprising cells as described herein such as particularly procoagulant cells as taught herein, wherein the arrangement is adapted for administration of said combination or pharmaceutical composition for example systemically, topically, within an organ or tissue. For example, a suitable surgical instrument may be capable of injecting a liquid composition comprising the combination or pharmaceutical composition taught herein, such as systemically, topically, within an organ or tissue.

Cells having procoagulant activity as intended throughout this specification encompass any cells which are capable of activating the coagulation cascade and to induce coagulation or clot formation. Procoagulant activity may be conveniently determined using any known coagulation test, such as without limitation thromboelastometry.

For example, cells may be denoted as having procoagulant activity in the sense of the present invention when, in a standard thromboelastometry test, the cells display clotting time (CT) significantly shorter ($p<0.05$ applying a suitable test of statistical significance) than a negative control without addition of cells. Whereas thromboelastometry represents a standard laboratory technique, for reasons of further guidance suitable thromboelastometry for testing the procoagulant nature of the cells as intended herein may be as follows:

Measurements is performed on a ROTEM® delta analyser (Pentapharm, Munich, Germany). ROTEM® assesses the kinetics and quality of clot formation and clot lysis in real-time. The clotting time (CT) is defined as the period of time from the start of the analysis until the start of clot formation, until the 2 mm amplitude is reached. After a short rest period, 300 µl of whole blood is pipetted into a cup pre-warmed at 37° C. Suspended cells (5×10exp5) are subsequently added to whole blood (negative control: equal volume of suspension medium without any suspended cells). 20 µl of trigger reagent containing tissue factor (TF) at final dilution 1:17000/0.35 pM (such as Innovin, Siemens, Marburg, Germany) diluted in Owren buffer (such as obtainable from Clin-Tech Ltd, UK) is added to the cell-blood mixture followed by addition of 20 µl of 0.2 M CaCl2. After calcium addition, measurements starts automatically. If no coagulation is observed after 1800 sec, thromboelastometry is stopped.

As intended herein, cells as intended herein such as particularly cells having procoagulant activity may be of any origin and/or differentiation state. Preferably, the cells as intended herein such as cells having procoagulant activity are selected from the group consisting of stem cells and progenitor cells. More preferably, the cells as intended herein such as cells having procoagulant activity are mesenchymal stem cells. Also preferably, the cells as intended herein such as cells having procoagulant activity are adult liver-derived progenitor or stem cells.

In an embodiment, the cells as intended herein such as cells having procoagulant activity are adult-derived human liver stem cells as generally described in WO 2007/071339; more particularly, human progenitor or stem cells originated from adult liver which express alpha-smooth muscle actin (ASMA) and albumin (ALB) and do not express cytokeratin-19 (CK-19) as described therein; even more particularly, human progenitor or stem cells originated from adult liver which express CD90, CD73, CD44, vimentin, ASMA and ALB and optionally express CYP3A4 and do not express CK-19 as described therein; yet more particularly, adult-derived human liver stem cells (ADHLSC) as described by Najimi et al., Cell Transplant, 2007, vol. 16, 717-28; and still more particularly cells as deposited by the Applicant of WO 2007/071339 on Feb. 20, 2006 under the Budapest Treaty with the Belgian Coordinated Collections of Microorganisms (BCCM/LMBP) under accession number LMBP 6452CB.

In an embodiment, the cells as intended herein such as cells having procoagulant activity are non-oval adult human liver-derived pluripotent progenitor cells as generally described in WO 2006/126236; more particularly, a non-oval human liver pluripotent progenitor cell line isolated from adult tissue which expresses hepatic cell markers and which is capable of differentiating into mature liver cells, insulin-producing cells, osteogenic cells and epithelial cells, or also particularly, a non-oval human liver pluripotent progenitor cell line isolated from adult tissue which expresses hepatic cell markers and which is capable of differentiating into mature liver cells, insulin-producing cells, osteogenic cells and endothelial cells, as described therein; even more particularly human liver stem cells (HLSC) as described by Herrera et al. Stem Cells, 2006, vol. 24, 2840-50.

Without wishing to be bound by any theory, it is believed that the expression of tissue factor (also known as platelet tissue factor, factor III, thrombokinase or CD142) by the cells having procoagulant activity is at least in part causative of the procoagulant activity of said cells (see, e.g., Beuneu et al. 2004, Moberg et al. 2002 and Stéphenne et al. 2007 supra). Accordingly, in an embodiment, the cells having procoagulant activity express tissue factor.

The inventors have further realised that particularly preferred procoagulant cells as used herein may comprise a procoagulant activity component independent of the expression of tissue factor (TF) by the cells. More specifically, such procoagulant cells will at least partly (e.g., only partly or wholly) retain their procoagulant activity as measured by thromboelastometry in Factor VII deficient plasma, or as measured by thromboelastometry in blood or normal plasma when TF activity is blocked, such as by pre-incubation of cells with anti-TF antibody. Without wishing to be bound by theory, the measurable procoagulant activity of cells in factor VII deficient plasma may at least in part also be related to residual small amounts of factor VII.

The inventors have further realised that particularly preferred procoagulant cells as used herein may comprise a procoagulant activity component resistant to heparin. More specifically, such procoagulant cells will at least partly (e.g., only partly or wholly) retain their procoagulant activity as measured by thromboelastometry in the presence of heparin alone (i.e., in the absence of thrombin activator), such as particularly in the presence of unfractionated heparin, enoxaparin or fondaparinux, particularly at concentrations of 10 UI/ml, 1 UI/ml and 0.34 mg/l, respectively. Hence, in further preferred embodiments, procoagulant cells as used herein may comprise a procoagulant activity component independent of the expression of tissue factor (TF) by the cells and may comprise a procoagulant activity component resistant to heparin.

An antithrombin activator as intended throughout this specification encompasses any agent capable of increasing the binding of antithrombin to any one or more of its targets.

In an embodiment, the antithrombin activator is selected from the group consisting of unfractionated heparin and low molecular weight heparin, preferably unfractionated heparin.

A thrombin inhibitor as intended throughout this specification is an agent capable of directly binding to thrombin and inhibiting or preventing thrombin-mediated fibrinogen activation.

In an embodiment, the thrombin inhibitor is selected from the group consisting of bivalirudin and hirudin, preferably bivalirudin. Advantageously, bivalirudin has a comparably short half live of about 35 to about 40 minutes, thereby allowing for a prompt return of a subject to a normal haemostasis status.

The above and additional aspects, preferred embodiments and features of the invention are described in the following sections and in the appended claims. Each aspect, embodiment or feature described herein may be combined with any other aspect(s), embodiment(s) or feature(s) unless clearly indicated to the contrary. In particular, any feature specified herein, and particularly any feature indicated as being preferred or advantageous, may be combined with any other feature(s) specified herein, and particularly with any other feature(s) indicated as being preferred or advantageous. The subject matter of appended claims is hereby specifically incorporated in this specification.

BRIEF DESCRIPTIONS OF THE FIGURES

FIG. 1 Clotting time (CT) essayed by ROTEM after recalcification, with and without added Tissue Factor (Ex- Tem 20 µl), of citrated whole blood (300 µl) in presence or not of cells suspended in human albumin 5%. Hep: Hepatocytes (white), ALDSC: Adult-derived human liver mesenchymal stem cells (black), A: human albumin 5%. ALDSC vs hepatocytes: Mann-Whitney test *p<0.05; ALDSC vs hepatocytes vs control: Kruskal-Wallis test ***p<0.001.

Figure 2:
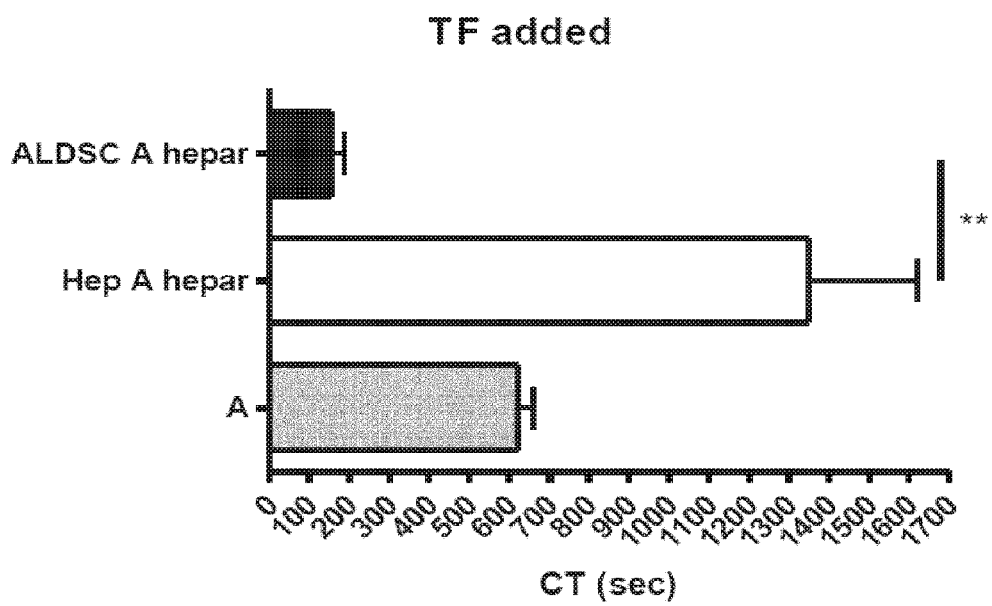

FIG. 2 Clotting time (CT) essayed by ROTEM after recalcification, with added Tissue Factor (ExTem 20 µl), of citrated whole blood (300 µl) in presence or not of cells suspended in human albumin 5% and heparin 10 Ul/ml (hepar). Hep: Hepatocytes (white), ALDSC: Adult-derived human liver mesenchymal stem cells (black), A: human albumin 5%. ALDSC vs hepatocytes: Mann-Whitney test p<0.01; ALDSC vs hepatocytes vs control: Kruskal-Wallis test *p<0.001.

Figure 3:
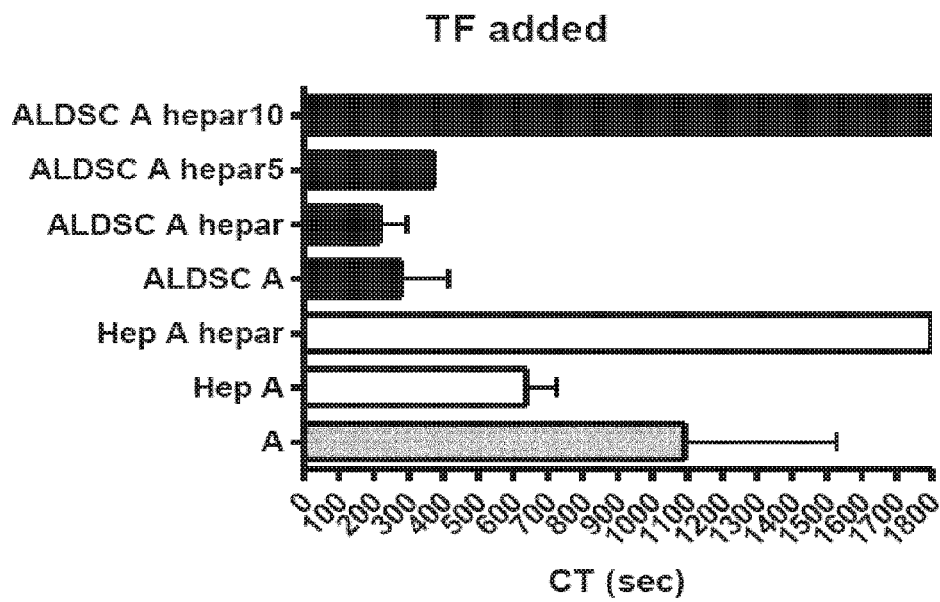

FIG. 3 Clotting time (CT) essayed by ROTEM after recalcification, with added Tissue Factor (ExTem 20 µl), of plasma (300 µl) obtained after 30 min incubation of citrated blood in presence or not of cells suspended in human albumin 5% and heparin (hepar) (10-50-100 Ul/ml). Hep: Hepatocytes (white), ALDSC: Adult-derived human liver mesenchymal stem cells (black), A: human albumin 5%.

Figure 4:
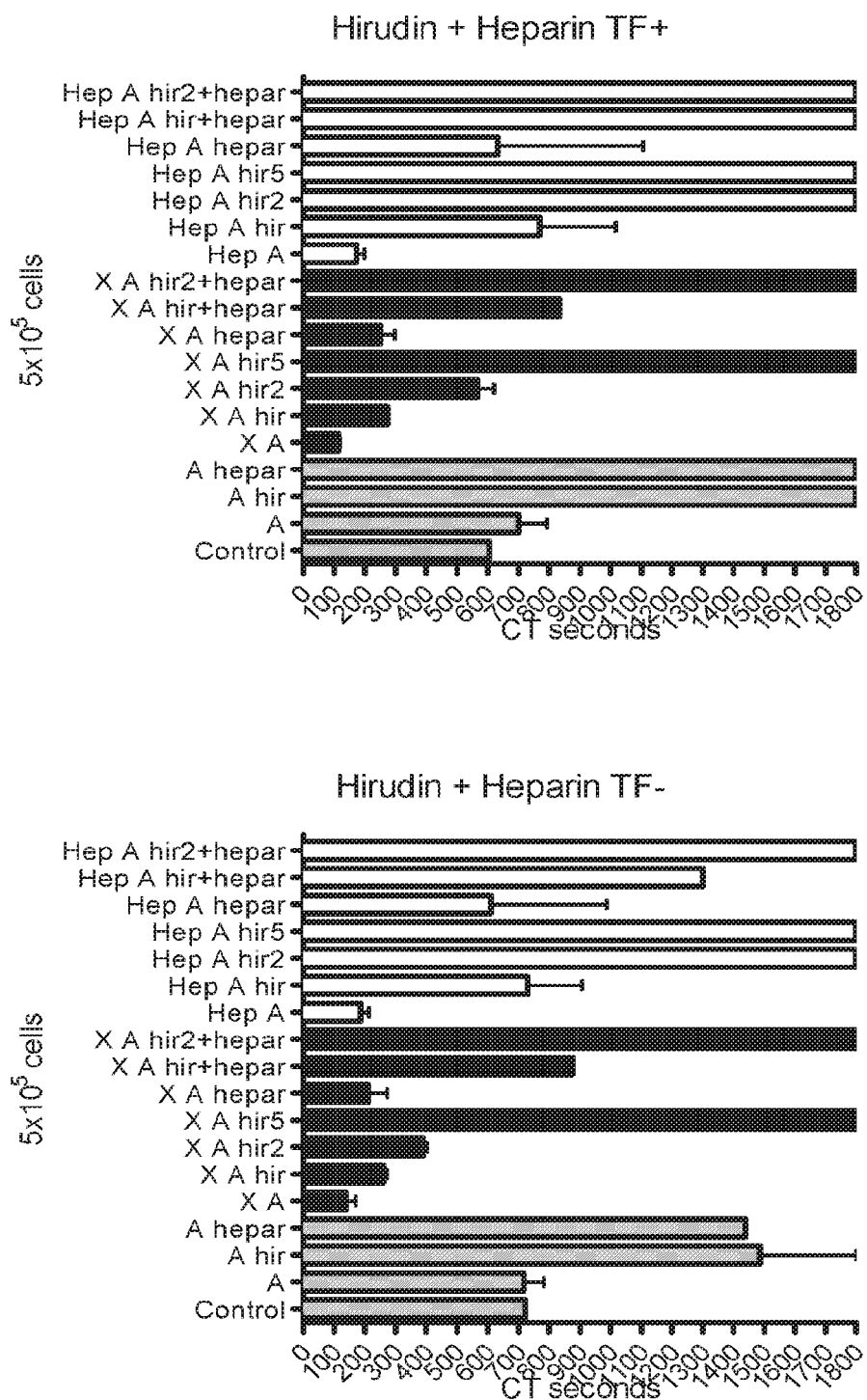

FIG. 4 Clotting time (CT) essayed by ROTEM, after recalcification, with and without added Tissue Factor (ExTem 20 µl), of citrated whole blood (300 µl) in presence or not of cells. Hep: Hepatocytes (white), ALDSC: Adult-derived human liver mesenchymal stem cells (black), A: human albumin 5%, hir, hir2, hir5: hirudin at 1, 2, 5-fold the bolus concentration in clinical use (0.4 mg/kg); hepar: heparin 10 Ul/ml in cell suspension; Control: whole blood.

Figure 5:
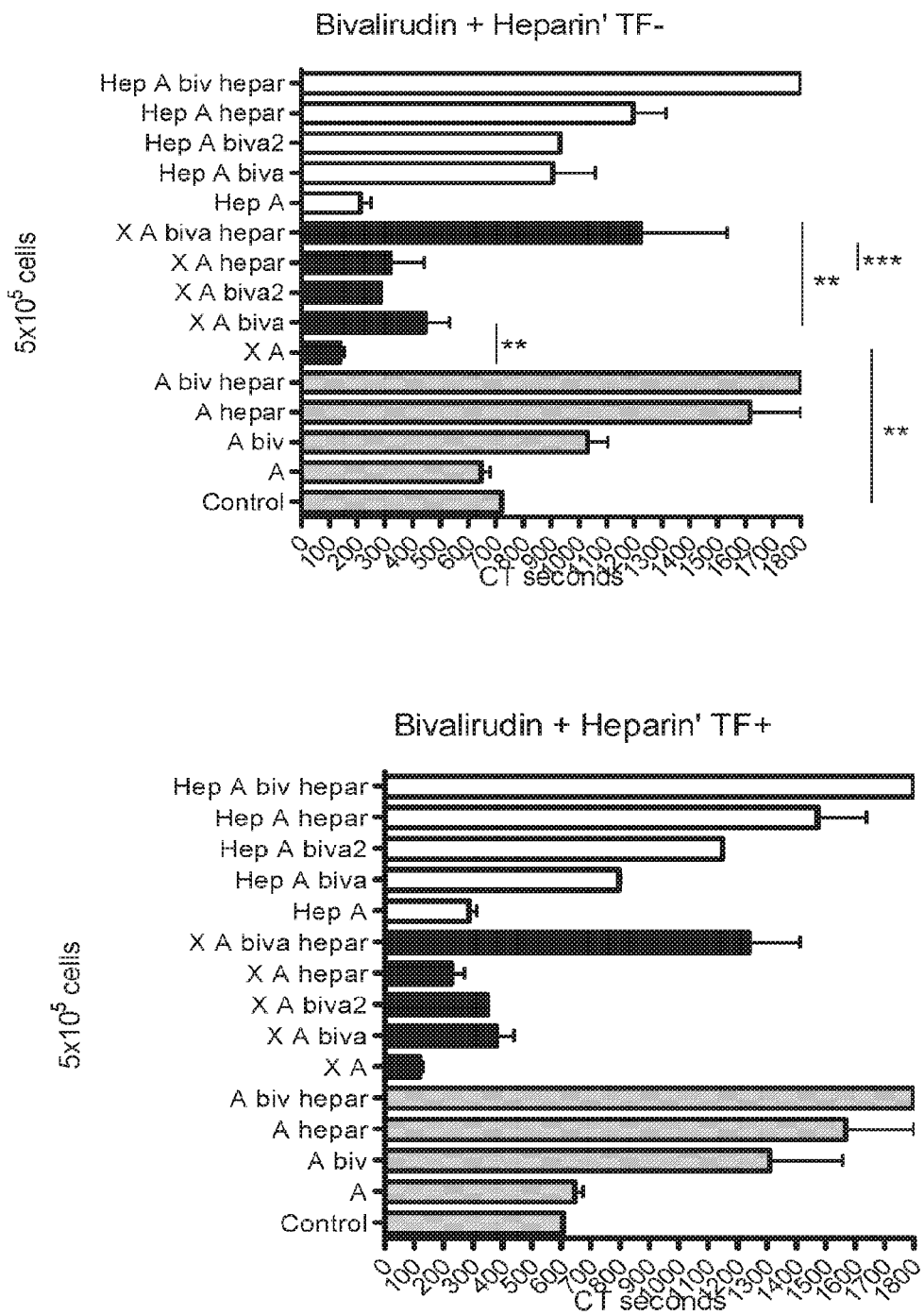

FIG. 5 Clotting time (CT) essayed by ROTEM after recalcification, with and without added Tissue Factor (ExTem 20 µl), of citrated whole blood (300 µl) in presence or not of cells. Hep: Hepatocytes (white), ALDSC: Adult-derived human liver mesenchymal stem cells s (black), A: human albumin 5%, biv, biv2: bivalirudin at 1, 2-fold the bolus concentration in clinical use (0.75 mg/kg); hepar: heparin 10 Ul/ml in cell suspension; Control: whole blood. ALDSC vs ALDSC biva: Mann-Whitney test p<0.01; A vs ALDSC biva: Mann-Whitney test p<0.01; ALDSC biva vs ALDSC biva hepar: Mann-Whitney test p<0.01; ALDSC hepar vs ALDSC biva hepar: Mann-Whitney test *p<0.001; ALDSC vs ALDSC biva vs ALDSC biva hepar: Kruskal-Wallis test ***p<0.001.

Figure 6:
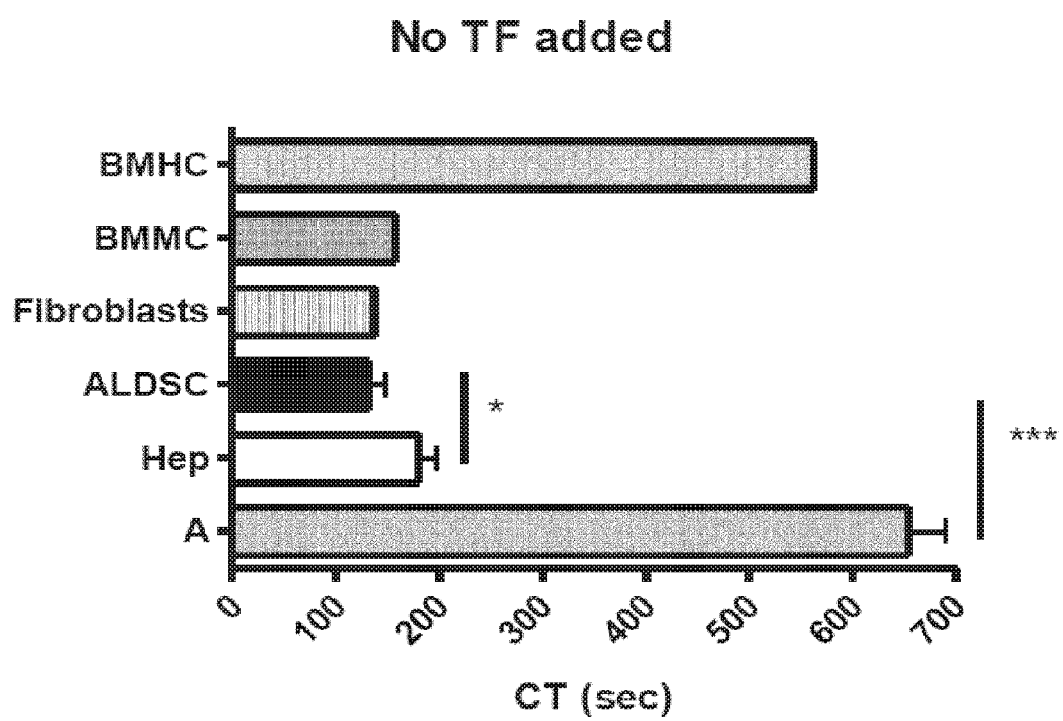

FIG. 6 Clotting time (CT) essayed by ROTEM after recalcification, without added Tissue Factor (ExTem 20 µl), of citrated whole blood (300 µl) in presence or not of cells. Hep: Hepatocytes (white), ALDSC: Adult-derived human liver mesenchymal stem cells (black), BMMC: bone marrow mesenchymal stem cells, BMHC: bone marrow haematopoietic stem cells, A: Albumin. ALDSC vs hepatocytes: Mann-Whitney test *p<0.05; A vs ALDSC: Mann-Whitney test ***p<0.001

FIG. 7 Clotting time (CT) essayed by ROTEM after recalcification, with added Tissue Factor (ExTem 20 µl), of citrated whole blood (300 µl) in presence or not of bone marrow haematopoietic stem cells suspended in human albumin 5% and heparin 10 Ul/ml (hepar).

Figure 8:
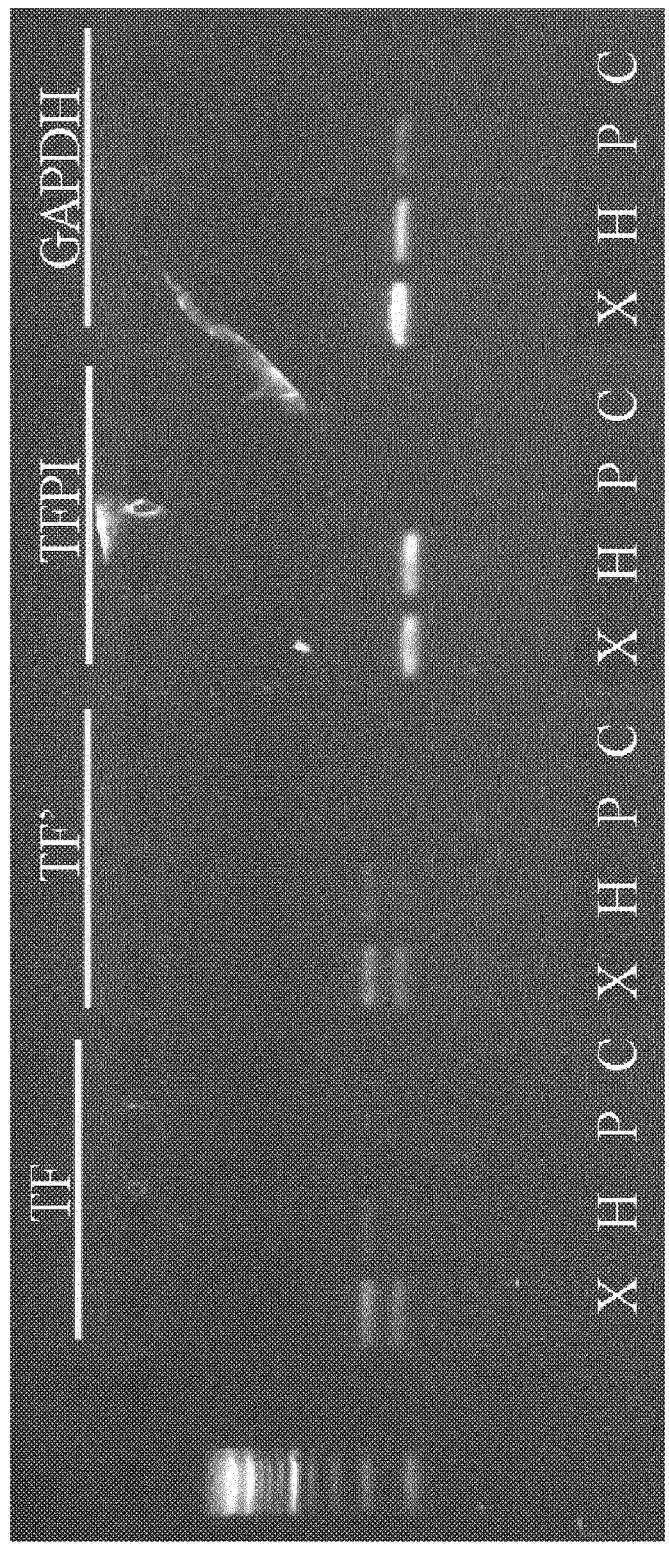

FIG. 8 Tissue factor and tissue factor pathway inhibitor (TFPI) mRNA expression in ALDSC evaluated by conventional RT-PCR. X=ALDSC cells; H=hepatocytes; P=PBMC; C=negative control; TF=Tissue factor (first set of primers); TF'=Tissue factor (second set of primers), TFPI=Tissue factor pathway inhibitor, GAPDH=Glyceraldehyde 3-Phosphate Dehydrogenase (technique control).

Figure 9:
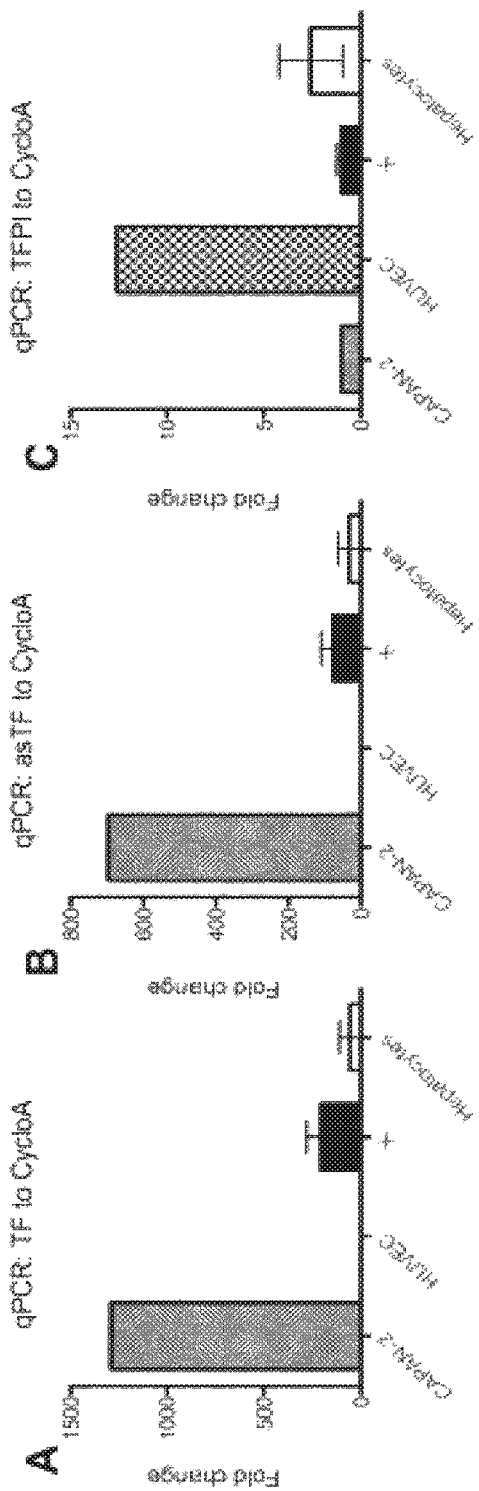

FIG. 9 Tissue factor mRNA (TF and as-TF) and TFPI expression of ALDSC evaluated by Real Time-PCR. Semi-quantitative expression of the mRNA of the TF gene (A), the alternatively splicing form as-TF (B) and the TFPI gene (C) among ALDSC (X) cells and hepatocytes. CAPAN-2 cells and HUVEC are positive control for TF, asTF and TFPI, respectively.

FIG. 10 (A) Clotting time (CT) essayed by ROTEM after recalcification, with added Tissue Factor (ExTem 20 µL), of citrated whole blood (300 µl) in presence or not of cells suspended in human albumin 5%. No coagulation is induced if absence of recalcification. Hepatocytes (white), hALPCs (black), Control (albumin) (grey). Hepatocytes vs. hALPCs p<0.001; Hepatocytes vs control p<0.001; hALPCs vs control p<0.01; hALPCs vs hepatocytes vs. control: Kruskal-Wallis test *p<0.001. (B) Clotting time (CT) essayed by ROTEM after recalcification, with added Tissue Factor (ExTem 20 µL), of plasma (300 µl) obtained from blood incubated in presence or not of cells suspended in human albumin 5%. Hepatocytes (white), hALPCs (black), Control (albumin) (grey). Hepatocytes vs. hALPCs p<0.05; Hepatocytes vs. control p<0.01; hALPCs vs. control p<0.01; hALPCs vs. hepatocytes vs. control: Kruskal-Wallis test *p<0.001. Procoagulant activity (PCA) of cells (hepatocytes and hALPCs) in blood and plasma is comparable when Innovin is not added.

Figure 11:
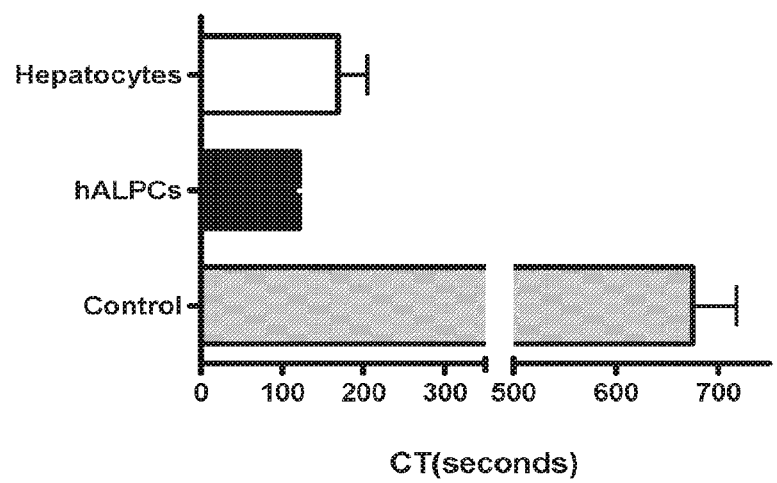

FIG. 11 Clotting time (CT) essayed by ROTEM after recalcification, without added Tissue Factor (ExTem 20 µL), of citrated whole blood (300 µl) in presence or not of cells suspended in human albumin 5%. No coagulation is induced if absence of recalcification. Hepatocytes (white), hALPCs (black)

Figure 12:
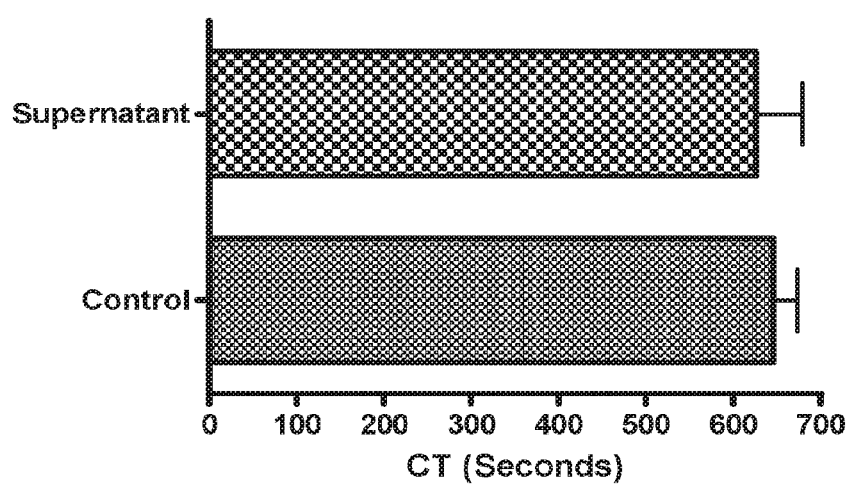

FIG. 12 Clotting time (CT) essayed by ROTEM after recalcification, with added Tissue Factor (ExTem 20 µL), of citrated whole blood (300 µl) in presence of supernatant of hALPCs culture. No coagulation is induced if absence of recalcification.

Figure 13:
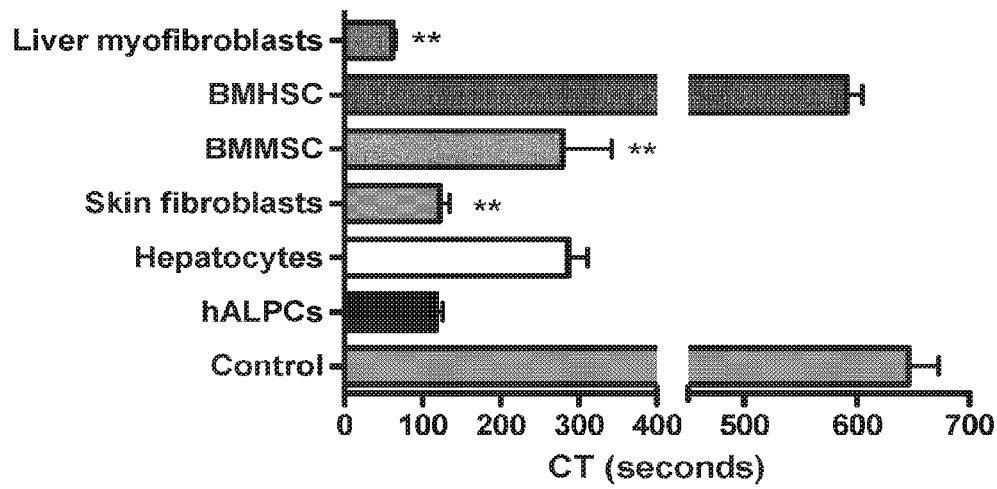

FIG. 13 Clotting time (CT) essayed by ROTEM after recalcification, with added Tissue Factor (ExTem 20 µL), of citrated whole blood (300 µl) in presence or not of hALPCs, hepatocytes, skin fibroblasts, bone marrow mesenchymal stem cells (BMMSC), bone marrow haematopoietic stem cells (BMHSC), liver myofibroblasts suspended in human albumin 5%. Fibroblasts vs. control p<0.01; BMMSC vs. control p<0.01; Liver myofibroblasts vs. control p<0.01.

Figure 14:
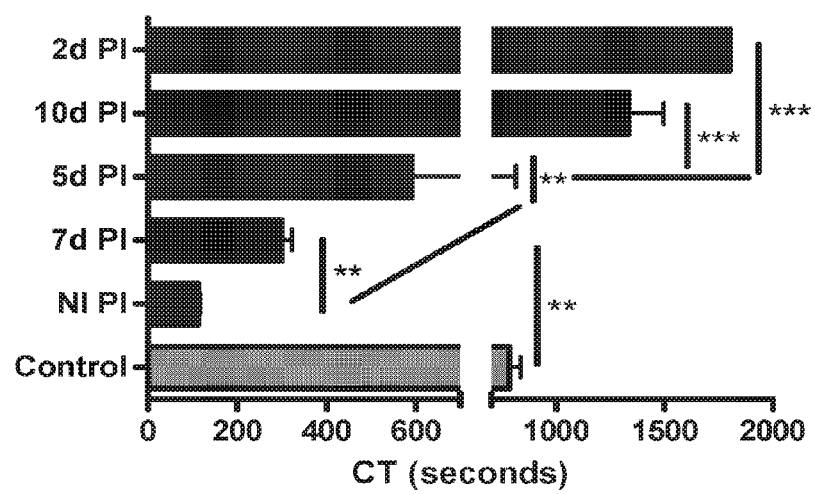

FIG. 14 Clotting time (CT) essayed by ROTEM after recalcification, with added Tissue Factor (ExTem 20 µL), of plasma (300 µl) deficient in coagulation factor VII, V, X and II (7d PI, 5d PI, 10d PI, 2d PI) in presence of cells suspended in human albumin 5%. hALPCs (black), Control (albumin) (grey). NI pI (normal plasma) vs. 7d PI p<0.01; 7d PI vs. control p<0.01; NI PI vs. 5d PI p<0.01; NI PI vs 10d PI p<0.001; NI PI vs. 2d PI p<0.001

FIG. 15 (A) Clotting time (CT) essayed by ROTEM after recalcification, with added Tissue Factor (ExTem 20 µL), of citrated whole blood (300 µl) in presence or not of hALPCs suspended in human albumin 5% with heparin (Hepar). At contrario, enoxaparin (Eno) or Fondaparinux (Fond) was extemporaneously added to blood in contact with cells suspended in albumin. hALPCs (black), Control (albumin) (grey).* as compared to hALPCs. f as compared to control. (B) Clotting time (CT) essayed by ROTEM after recalcification, with added Tissue Factor (ExTem 20 µL), of citrated whole blood (300 µl) in presence or not of hALPCs suspended in human albumin 5%. Bivalirudin (Biva) or Hirudin (Hir) was extemporaneously added to blood. hALPCs (black), Control (albumin) (grey).* as compared to hALPCs.

f as compared to control. (C) Clotting time (CT) essayed by ROTEM after recalcification, with added Tissue Factor (ExTem 20 µL), of citrated whole blood (300 µl) in presence or not of hepatocytes suspended in human albumin 5% with heparin (Hepar). At contrario, enoxaparin (Eno) or Fondaparinux (Fond) was extemporaneously added to blood in contact with cells suspended in albumin. Hepatocytes (white), Control (albumin) (grey). * as compared to hepatocytes. f as compared to control. (D) Clotting time (CT) essayed by ROTEM after recalcification, with added Tissue Factor (ExTem 20 µL), of citrated whole blood (300 µl) in presence or not of hepatocytes suspended in human albumin 5%. Bivalirudin (Biva) or Hirudin (Hir) was extemporaneously added to blood. Hepatocytes (white), Control (albumin) (grey). * as compared to hepatocytes. f as compared to control FIG. 16 (A) Clotting time (CT) essayed by ROTEM after recalcification, with added Tissue Factor (ExTem 20 µL), of citrated whole blood (300 µl) in presence or not of hALPCs suspended in human albumin 5% with heparin (Hepar) or with Enoxaparin (Eno) or Fondaparinux (Fond) extemporaneously added to blood. Combination of anticoagulant drugs was obtained when bivalirudin (Biva) was extemporaneously added to blood. hALPCs (black), Control (albumin) (grey). * as compared to hALPCs. f as compared to control. $ as compared to bivalirudin. (B). Clotting time (CT) essayed by ROTEM after recalcification, with added Tissue Factor (ExTem 20 µL), of citrated whole blood (300 µl) in presence or not of hepatocytes suspended in human albumin 5% with heparin (Hepar) or with Enoxaparin (Eno) or Fondaparinux (Fond) extemporaneously added to blood. Combination of anticoagulant drugs was obtained when bivalirudin (Biva) was extemporaneously added to blood. Hepatocytes (white), Control (albumin) (grey). * as compared to hepatocytes. f as compared to control. $ as compared to bivalirudin FIG. 17 Immunofluorescence for TF was performed on hALPCs (A) placed on cover slips and fixed by paraformaldehyde (magnification 20×). The nuclei were revealed by DAPI (blue staining). (B) Negative control (without primary antibody).

Figure 18:
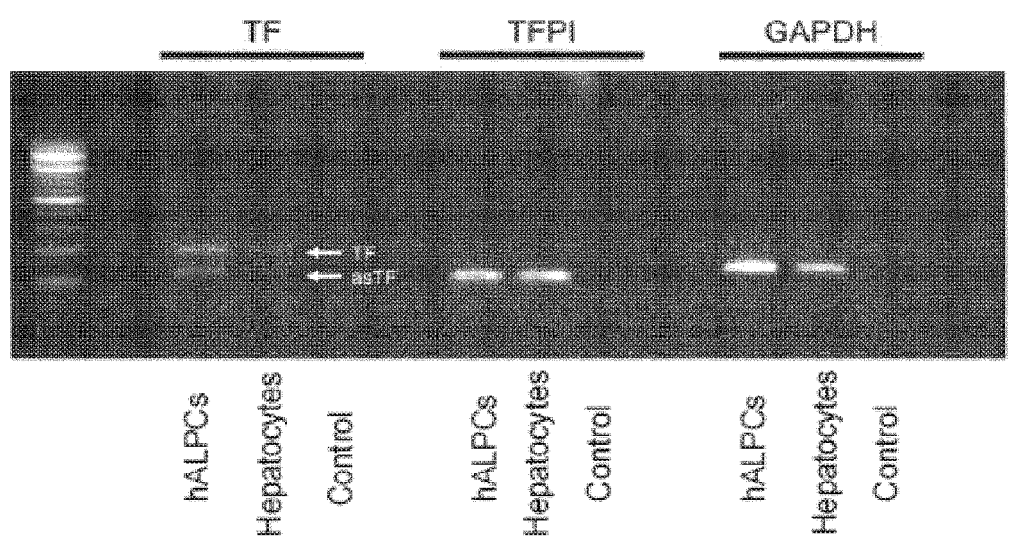

FIG. 18 Tissue factor and tissue factor pathway inhibitor (TFPI) mRNA expression in hALPCs and hepatocytes evaluated by conventional RT-PCR. Tissue factor (TF), alternatively spliced Tissue Factor (asTF), Tissue factor pathway inhibitor (TFPI), Glyceraldehyde 3-Phosphate Dehydrogenase (GAPDH) (technique control).

Figure 19:
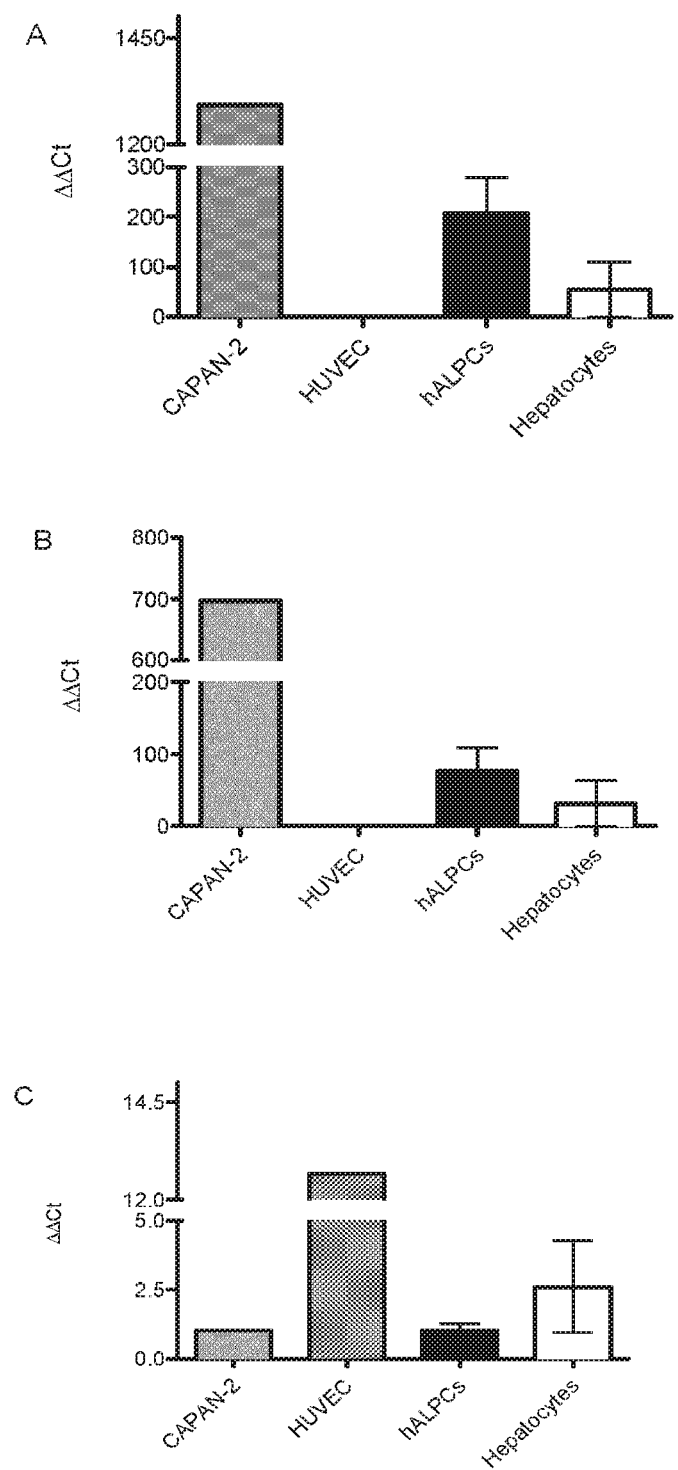

FIG. 19 Tissue factor mRNA (TF and as-TF) and TFPI expression of hALPCs and hepatocytes evaluated by Real Time-PCR. Semi-quantitative expression of the mRNA of the TF gene (A), the alternatively splicing form as-TF (B) and the TFPI gene (C) among hALPCs cells and hepatocytes. CAPAN-2 cells and HUVEC are positive control for TF, asTF and TFPI, respectively.

Figure 20:
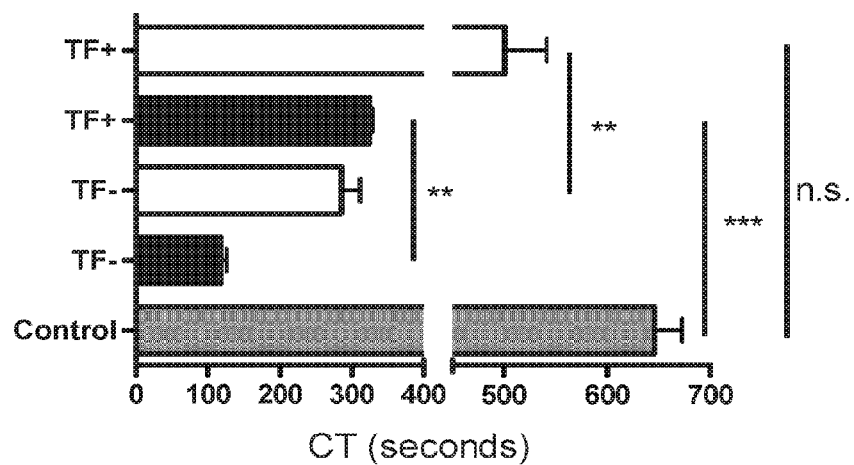
Figure 21:
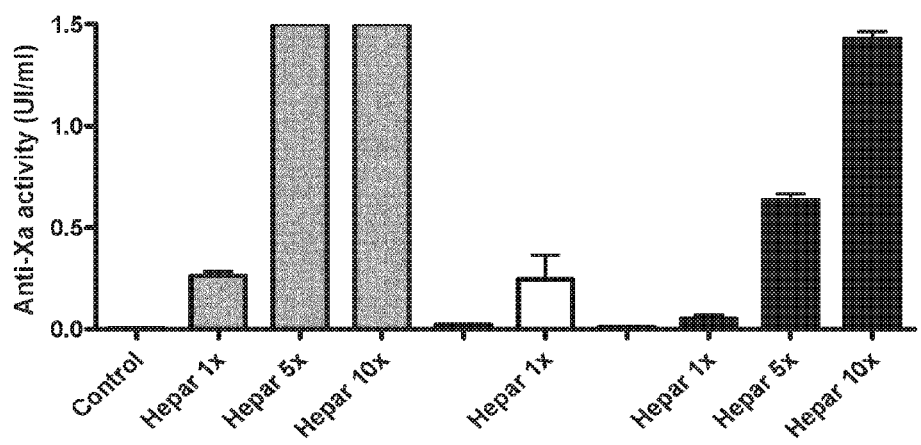

FIG. 20 Clotting time (CT) essayed by ROTEM after recalcification, with added Tissue Factor (ExTem 20 µL), of citrated whole blood (300 µl) in presence or not of cells suspended in human albumin 5% after incubation of cells with TF antibody (TF+) or not (TF−). Hepatocytes (white), hALPCs (black), Control (albumin) (grey). hALPCs TF− vs hALPCs TF+p<0.01; Hepatocytes TF− vs Hepatocytes TF+p<0.01; hALPCs TF+vs control p<0.001; Hepatocytes vs control non significant FIG. 21 After 30 min incubation of cells suspended in albumin supplemented or not with heparin (Hepar) (10 Ul/ml, 50 Ul/ml, and 100 Ul/ml) in blood, anti-Xa activity (Ul/ml) was measured in plasma obtained after blood centrifugation. hALPCs (Black), Hepatocytes (Hep) (White), Control (Grey)

Figure 22:
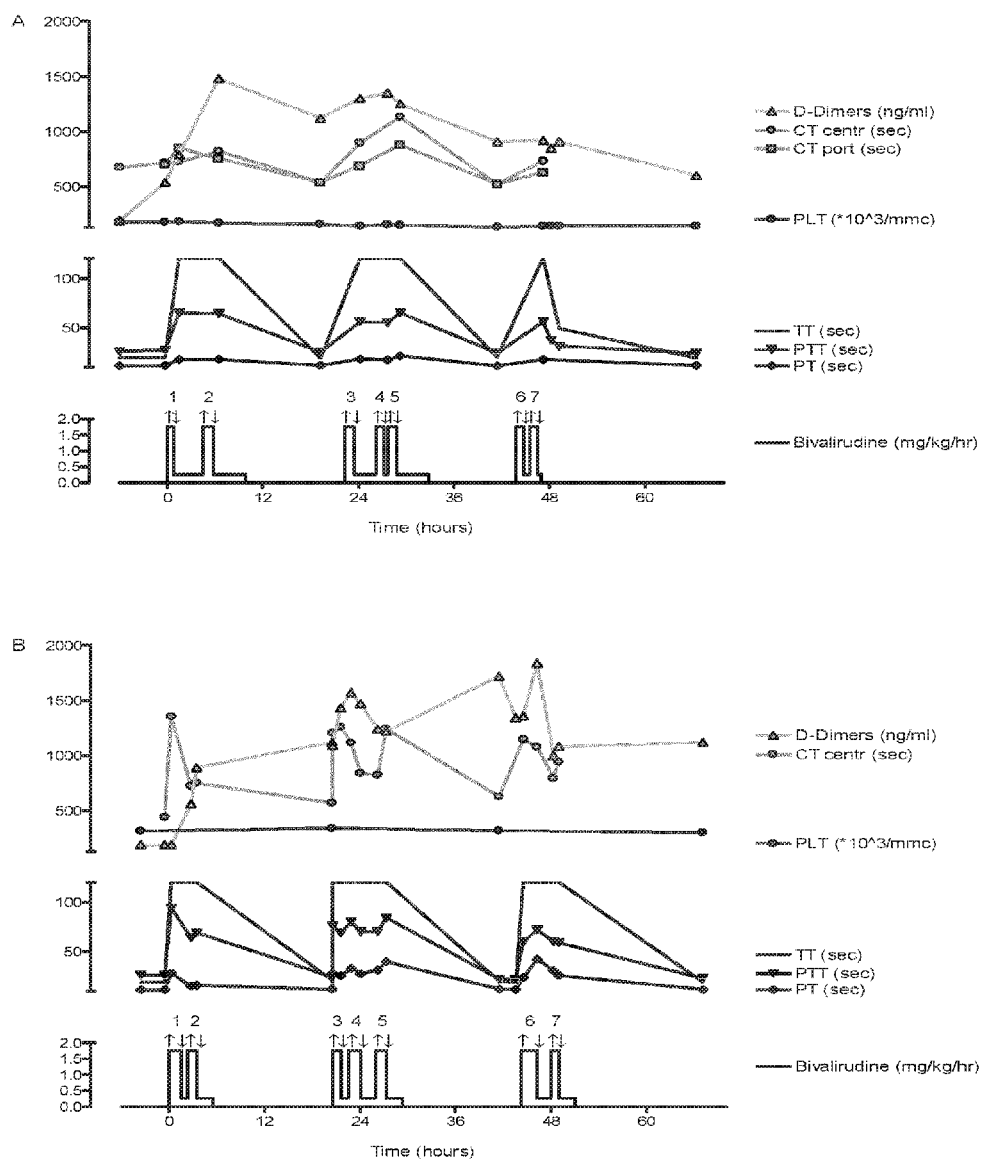

FIG. 22 During cell infusion, the patients receive bivalirudin (1.75 mg/kg). Between consecutive cell infusions, the dose was decreased to 0.25 mg/kg for 2 to 4 hours. Coagulation tests including thromboelastometry (CT in portal vein (port) or via the central line (centr)), platelets (PLT) (normal values: 150-350 10exp3/µl) and D-Dimers levels (normal values: <500 ng/ml), Thrombin time (TT, normal values: 15-24 sec), Prothrombin time (PT, normal values: 9-14 sec) and Partial thromboplastin time (PTT, normal values: 20-33 sec) were repetitively performed before, 20 min after beginning and at the end of each infusion. A Crigler Najjar patient; B Glycogenosis type 1a patient.

FIG. 23 (A) Clotting time (CT) essayed by ROTEM after recalcification, with added Tissue Factor (ExTem 20 µL), of citrated whole blood (300 µl) in presence or not of hALPCs (Black) suspended in human albumin 5% with or without heparin (Hepar) at several concentrations (Hepar-10 Ul/ml, Hepar 5×-50 Ul/ml, Hepar10×-100 Ul/ml). Control (albumin) (grey). Control vs. hALPCs Hepar 5× p<0.01. (B) Clotting time (CT) essayed by ROTEM after recalcification, with added Tissue Factor (ExTem 20 µL), of citrated whole blood (300 µl) in presence or not of hALPCs (Black) suspended in human albumin 5% with or without fondaparinux (Fond), enoxaparin (Eno) at normal concentration or increased at 5× the normal concentration. Control (albumin) (grey). Control vs. hALPCs Fond 5×, p<0.01; Control vs. hALPCs Eno 5×, p<0.01; Fond vs. Fond 5×, n.s.; Eno vs. Eno 5×, n.s.

Figure 24:
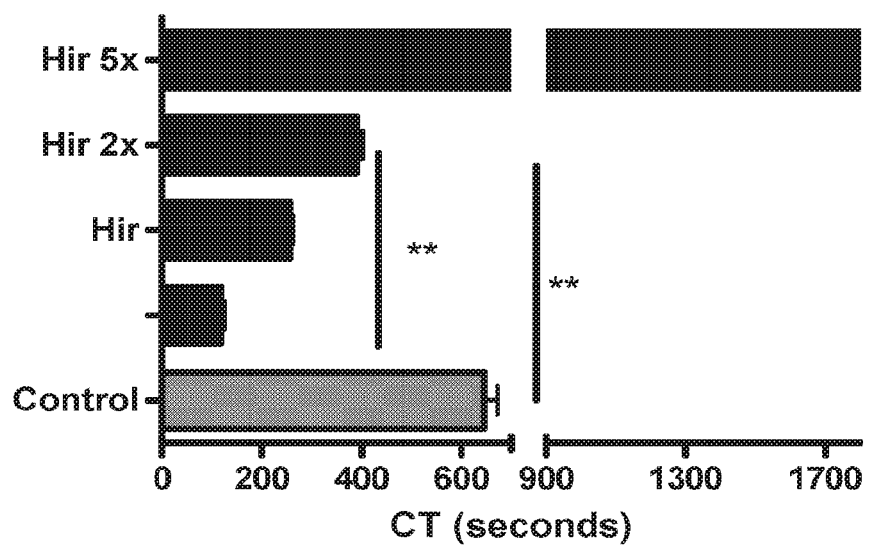

FIG. 24 Clotting time (CT) essayed by ROTEM after recalcification, with added Tissue Factor (ExTem 20 µL), of citrated whole blood (300 µl) in presence or not of hALPCs suspended in human albumin 5%. Increased concentration of hirudin (Hir) (2× (Hir 2×) or 5× (Hir 5×)) was extemporaneously added to blood. hALPCs (black), Control (albumin) (grey). Control vs. hALPCs Hir 2×, p<0.01; hALPCs vs. hALPCs Hir 2×, p<0.01; hALPCs Hir vs. hALPCs Hir 2×, n.s.

Figure 25:
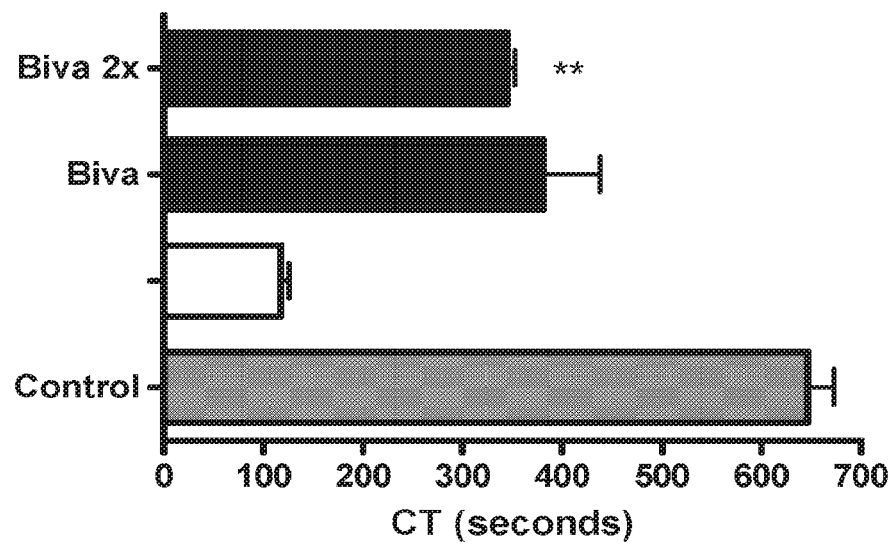

FIG. 25 Clotting time (CT) essayed by ROTEM after recalcification, with added Tissue Factor (ExTem 20 µL), of citrated whole blood (300 µl) in presence or not of hALPCs suspended in human albumin 5%. Increased concentration of bivalirudin (Biva) (2× (Biva 2×)) was extemporaneously added to blood. hALPCs (black), Control (albumin) (grey). Control vs. hALPCs Biva 2×, p<0.01

Figure 26:
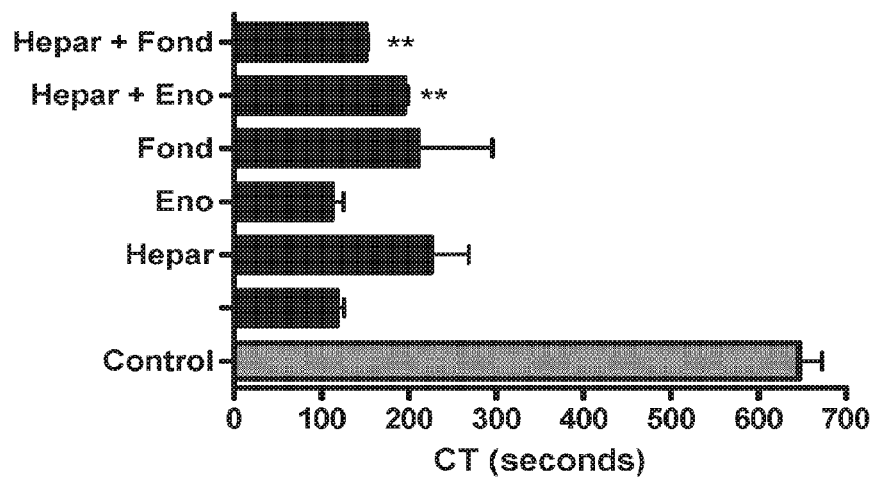

FIG. 26 Clotting time (CT) essayed by ROTEM after recalcification, with added Tissue Factor (ExTem 20 µL), of citrated whole blood (300 µl) in presence or not of hALPCs suspended in human albumin 5% with or without heparin (Hepar). Enoxaparin (Eno) or fondaparinux (Fond) was extemporaneously added to blood with cells suspended or not in heparin hALPCs (black), Control (albumin) (grey). Control vs hALPCs Hepar+Eno, p<0.01; Control vs. hALPCs Hepar+Fond, p<0.01

Figure 27:
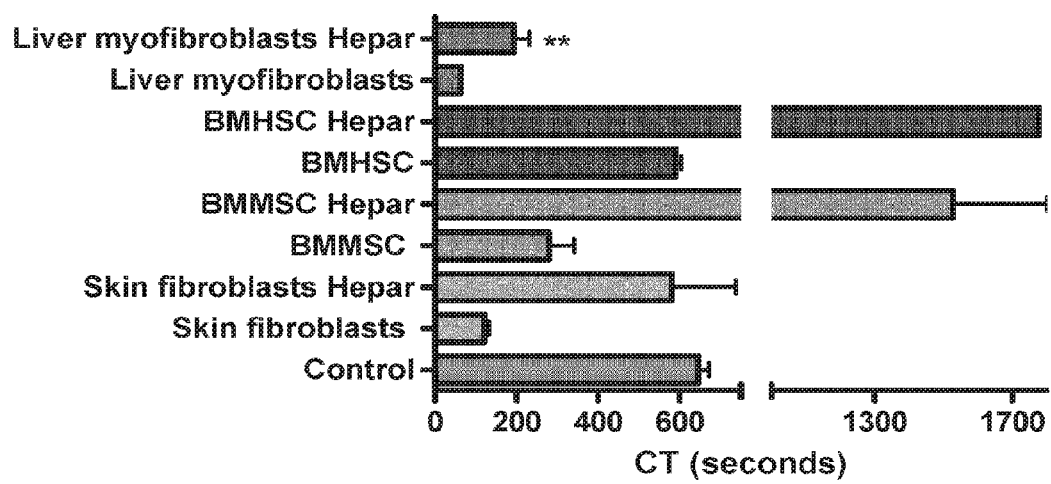

FIG. 27 Clotting time (CT) essayed by ROTEM after recalcification, with added Tissue Factor (ExTem 20 µL), of citrated whole blood (300 µl) in presence or not of hALPCs, hepatocytes, skin fibroblasts, bone marrow mesenchymal stem cells (BMMSC), bone marrow haematopoietic stem cells (BMHSC), liver myofibroblasts suspended in human albumin 5% with or without heparin (10 Ul/ml) (Hepar). Fibroblasts Hepar vs. control n.s.; Liver myofibroblasts Hepar vs. control p<0.01

Figure 28:
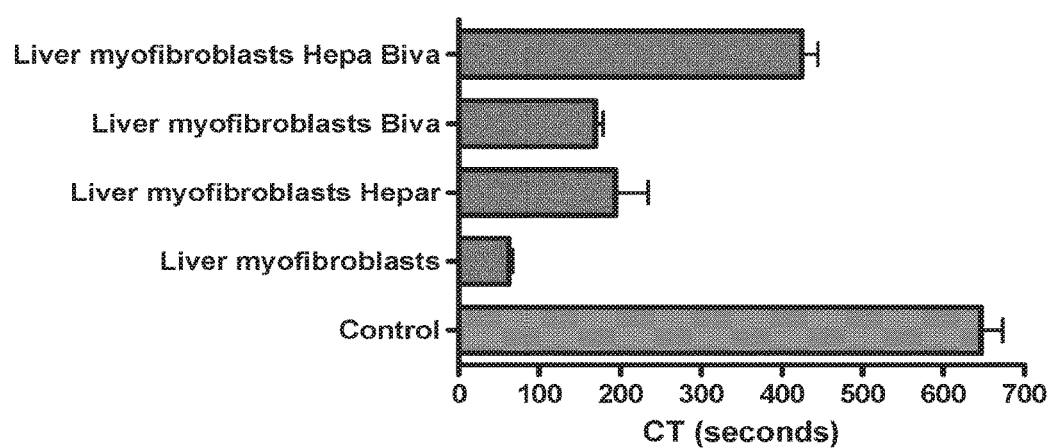

FIG. 28 Clotting time (CT) essayed by ROTEM after recalcification, with added Tissue Factor (ExTem 20 µL), of citrated whole blood (300 µl) in presence or not liver myofibroblasts suspended in human albumin 5% with or without heparin (10 UI/ml) (Hepar). Combination of anticoagulant drugs was obtained when bivalirudin (Biva) was extemporaneously added to blood in contact with cells suspended in heparin.

DETAILED DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The term also encompasses "consisting of" and "consisting essentially of".

The recitation of numerical ranges by endpoints includes all numbers and fractions subsumed within the respective ranges, as well as the recited endpoints.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

Preferred cells in the combinations, compositions, kits, methods and uses as described herein are adult liver progenitor cells, mesenchymal stem cells (preferably bone marrow mesenchymal stem cells), skin fibroblasts, or liver myofibroblasts, more preferably adult liver progenitor cells or liver myofibroblasts, most preferably adult liver progenitor cells.

As used herein, the term "cells having procoagulant activity" encompasses cells which are capable of or have the propensity to activate the coagulation cascade and induce coagulation or clot formation.

Cells having procoagulant activity as intended herein may trigger the coagulation cascade at any stage, whereby ultimately fibrinogen is converted to fibrin, which cross-links into a clot. By means of example and without limitation, cells having procoagulant activity may express tissue factor, the expression of which may trigger the activation of factor X to factor Xa, which in its turn, via cleavage of prothrombin to thrombin, leads to clot formation via thrombin-mediated fibrinogen conversion to fibrin. The term "cells with procoagulant activity" can be used interchangeably with "procoagulant cells". The term "procoagulant activity" can be used interchangeably with "prothrombotic activity". While procoagulant activity of cells may be determined by the presence (or absence) of specific cell characteristics, such as for instance, and without limitation, the expression of specific markers, such as tissue factor, procoagulant activity of cells may equally be determined by techniques such as for instance, and without limitation, thromboelastometry. In brief, thromboelastometry is an established viscoelastic method for haemostasis testing in blood (or by extension any sample containing the components of the coagulation cascade, such as plasma), whereby elasticity changes in a sample are correlated with clot formation. By means of example, and without limitation, thromboelastometry measurements can be performed on a ROTEM® delta analyser (Pentapharm, Munich, Germany). Alternatively, procoagulant activity may be measured by the tubing loop method, as described in Johansson et al. (Diabetes, 2005, 54:1755-1762). Procoagulant activity may also for instance be apparent from and determined by specific cytokine profiles (reviewed for instance in van der Poll et al. Regulatory role of cytokines in disseminated intravascular coagulation. Semin Thromb Hemost. 2001, 27:639-51).

Cells having procoagulant activity as intended herein may be particularly suited or configured for transplantation thereof. The cells may be allogeneic cells (i.e., isolated from a different subject, but of the same species, as the subject to which the cells are to be transplanted) or alternatively may be autologous cells (i.e. isolated from the same subject as the subject to which the cells are to be transplanted), or may even be xenogeneic cells (i.e., isolated from a subject of a different species than the subject to which the cells are to be transplanted). The procoagulant cells may be primary cells or alternatively may be cells that have been subject to manipulation in vitro. As used herein, the term "manipulation in vitro" refers to any kind of manipulation of the cells outside the body. Examples of such manipulations are, without limitation, administration of drugs or other compounds which elicit an effect in the cells; depletion of specific cell constituents; genetic manipulation; gene therapy; stable or transient transfection, (pseudo)viral infection, or transformation; differentiation; dedifferentiation; subcloning etc. It may be clear that regardless of the cell origin, the cells may be subjected to storage (e.g. cryopreservation) and/or proliferation or passaging before transplantation. Cells may be induced to express one or more specific proteins (whether or not own to the cell, i.e., autologous) or to increase or decrease (or completely or substantially completely block) the expression thereof. Alternative to manipulation in vitro, the cells to be transplanted may be subject to manipulation prior to isolation from the donor (e.g., drug treatment, gene therapy, etc.). Also, the cells having procoagulant activity may be a cell line.

In an embodiment, procoagulant cells as intended herein may be non-haematopoietic (stem) cells, as said cells tend to not display procoagulant activity.

Besides transplanting cells to restore or improve functionality provided thereby, in non-limiting examples, the cell product to be transplanted may include without limitation cancer cells (e.g., for study of cancer in animal models), cell-based vaccines or immunotolerance agents, etc.

Where desired, the cells may be stably or transiently transformed with nucleic acids of interest prior to introduction to the subject. Nucleic acid sequences of interest include, but are not limited to those encoding gene products that enhance the growth, differentiation and/or functioning of said cells. For example and without limitation, an expression system for a protein normally expressed by liver cells can be introduced in a stable or transient fashion for the purpose of treating diseases or conditions benefiting from expression of such a protein using so-transformed (preferably liver) cells, e.g., inborn errors of liver metabolism. Methods of cell transformation are known to those skilled in the art.

Cells as intended herein such as in particular procoagulant cells as intended herein may be preferably of animal origin, more preferably of warm-blooded animal, even more preferably of vertebrate, yet more preferably of mammalian, and still more preferably of primate origin, and specifically including cells of human or non-human mammal or primate origin. Preferred cells such as procoagulant cells are of human origin. The term "mammal" as used throughout this specification includes any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes.

Cells as intended herein such as in particular procoagulant cells as intended herein may encompass without limitation progenitor cells, stem cells or partly or fully differentiated cells, such as terminally differentiated cells (i.e., fully specialised cells that may be post-mitotic).

Preferably as intended herein, cells such as procoagulant cells, and particularly progenitor or stem cells, may be of adult origin (e.g., adult progenitor or stem cells) i.e., present in or obtained from (such as removed or isolated from) an organism at the foetal stage or more preferably after birth (postpartum).

By means of example and not limitation, adult origin of cells as intended herein, such as for example of adult liver progenitor cells, may refer to origin from neonatal tissue or from tissue at any subsequent developmental stage such as inter alia stages conventionally denoted in human development as infant, child, youth, adolescent or adult. For example, for human cells (such as human adult liver progenitor cells), adult origin may refer to origin from a tissue (such as liver tissue) at any time after birth, preferably full term, and may be, e.g., at least one month of age after birth, e.g., at least 2 months, at least 3 months, e.g., at least 4 months, at least 5 months, e.g., at least 6 months age after birth, such as, for example, 1 year or more, 5 years or more, at least 10 years or more, 15 years or more, 20 years or more, or 25 years or more of age after birth.

The terms "progenitor" or "progenitor cell" are synonymous and generally refer to an unspecialised or relatively less specialised and proliferation-competent cell which can under appropriate conditions give rise to at least one relatively more specialised cell type, such as inter alia to relatively more specialised progenitor cells or eventually to terminally differentiated cells. A progenitor cell may "give rise" to another, relatively more specialised cell when, for example, the progenitor cell differentiates to become said other cell without previously undergoing cell division, or if said other cell is produced after one or more rounds of cell division and/or differentiation of the progenitor cell.

The term "stem cell" generally refers to a progenitor cell capable of self-renewal, i.e., which can under appropriate conditions proliferate without differentiation. The term encompasses stem cells capable of substantially unlimited self-renewal, i.e., wherein at least a portion of the stem cell's progeny substantially retains the unspecialised or relatively less specialised phenotype, the differentiation potential, and the proliferation capacity of the mother stem cell; as well as stem cells which display limited self-renewal, i.e., wherein the capacity of the stem cell's progeny for further proliferation and/or differentiation is demonstrably reduced compared to the mother cell.

Progenitor or stem cells as intended herein may be pluripotent (i.e., capable under appropriate conditions of producing progeny of different cell types that are derivatives of all three germ layers, i.e., endoderm, mesoderm, and ectoderm, according to a standard art-accepted test, such as inter alia the ability to form a teratoma in SCID mice, or the ability to form identifiable cells of all three germ layers in tissue culture), multipotent (i.e., capable under appropriate conditions of producing progeny of at least three cell types from each of two or more different organs or tissues of an organism, wherein said cell types may originate from the same or from different germ layers, but not capable of giving rise to all of the cell types of an organism), or committed to only one or a few (e.g., one, two or three) cell lineages.

Prototype mammalian pluripotent stem cells (mPS) may be derived from any kind of mammalian embryonic tissue, e.g., embryonic, foetal or pre-foetal tissue. Included in the definition of mPS cells are embryonic stem cells of various types, exemplified without limitation by murine embryonic stem cells, e.g., as described by Evans & Kaufman 1981 (Nature 292: 154-6) and Martin 1981 (PNAS 78: 7634-8); rat pluripotent stem cells, e.g., as described by Iannaccone et al. 1994 (Dev Biol 163: 288-292); hamster embryonic stem cells, e.g., as described by Doetschman et al. 1988 (Dev Biol 127: 224-227); rabbit embryonic stem cells, e.g., as described by Graves et al. 1993 (Mol Reprod Dev 36: 424-433); porcine pluripotent stem cells, e.g., as described by Notarianni et al. 1991 (J Reprod Fertil Suppl 43: 255-60) and Wheeler 1994 (Reprod Fertil Dev 6: 563-8); sheep embryonic stem cells, e.g., as described by Notarianni et al. 1991 (supra); bovine embryonic stem cells, e.g., as described by Roach et al. 2006 (Methods Enzymol 418: 21-37); human embryonic stem (hES) cells, e.g., as described by Thomson et al. 1998 (Science 282: 1145-1147); human embryonic germ (hEG) cells, e.g., as described by Shamblott et al. 1998 (PNAS 95: 13726); embryonic stem cells from other primates such as Rhesus stem cells, e.g., as described by Thomson et al. 1995 (PNAS 92:7844-7848) or marmoset stem cells, e.g., as described by Thomson et al. 1996 (Biol Reprod 55: 254-259).

As noted, prototype "human ES cells" are described by Thomson et al. 1998 (supra) and in U.S. Pat. No. 6,200,806. The scope of the term covers pluripotent stem cells that are derived from a human embryo at the blastocyst stage, or before substantial differentiation of the cells into the three germ layers. ES cells, in particular hES cells, are typically derived from the inner cell mass of blastocysts or from whole blastocysts. Derivation of hES cell lines from the morula stage has been documented and ES cells so obtained can also be used in the invention (Strelchenko et al. 2004. Reproductive BioMedicine Online 9: 623-629). As noted, prototype "human EG cells" are described by Shamblott et al. 1998 (supra). Such cells may be derived, e.g., from gonadal ridges and mesenteries containing primordial germ cells from foetuses. In humans, the foetuses may be typically 5-11 weeks post-fertilisation.

Except where explicitly required otherwise, the term mPS cells may include primary tissue cells and established lines that bear phenotypic characteristics of the respective cells, and derivatives of such primary cells or cell lines that still have the capacity of producing progeny of each of the three germ layers.

Exemplary but non-limiting established lines of human ES cells include lines which are listed in the NIH Human Embryonic Stem Cell Registry (http://stemcells.nih.gov/research/registry), and sub-lines thereof, such as, lines hES-BGN-01, hESBGN-02, hESBGN-03 and hESBGN-04 from Bresagen Inc. (Athens, Ga.), lines Sahlgrenska 1 and Sahlgrenska 2 from Cellartis AB (Göteborg, Sweden), lines HES-1, HES-2, HES-3, HES-4, HES-5 and HES-6 from ES Cell International (Singapore), line Miz-hES1 from Miz-Medi Hospital (Seoul, Korea), lines I 3, I 3.2, I 3.3, I 4, I 6, I 6.2, J 3 and J 3.2 from Technion—Israel Institute of Technology (Haifa, Israel), lines HSF-1 and HSF-6 from University of California (San Francisco, Calif.), lines H1, H7, H9, H13, H14 of Wisconsin Alumni Research Foundation/WiCell Research Institute (Madison, Wis.), lines CHA-hES-1 and CHA-hES-2 from Cell & Gene Therapy Research Institute/Pochon CHA University College of Medicine (Seoul, Korea), lines H1, H7, H9, H13, H14, H9.1 and H9.2 from Geron Corporation (Menlo Park, Calif.), lines Sahlgrenska 4 to Sahlgrenska 19 from Göteborg University (Göteborg, Sweden), lines MB01, MB02, MB03 from Maria Biotech Co. Ltd. (Seoul, Korea), lines FCNCBS1, FCNCBS2 and FCNCBS3 from National Centre for Biological Sciences (Bangalore, India), and lines RLS ES 05, RLS ES 07, RLS ES 10, RLS ES 13, RLS ES 15, RLS ES 20 and RLS ES 21 of Reliance Life Sciences (Mumbai, India). Other exemplary established hES cell lines include those deposited at the UK Stem Cell Bank (http://www.uk-stemcellbank.org.uk/), and sub-lines thereof, e.g., line WT3 from King's College London (London, UK) and line hES-NCL1 from University of Newcastle (Newcastle, UK) (Strojkovic et al. 2004. Stem Cells 22: 790-7). Further exemplary ES cell lines include lines FC018, AS034, AS034.1, AS038, SA111, SA121, SA142, SA167, SA181, SA191, SA196, SA203 and SA204, and sub-lines thereof, from Cellartis AB (Göteborg, Sweden).

Further within the term mammalian pluripotent stem cells are such mPS cells obtainable by manipulation, such as inter alia genetic and/or growth factor and/or small molecule mediated manipulation, of non-pluripotent mammalian cells, such as somatic and particularly adult somatic mammalian cells, including the use of induced pluripotent stem (iPS) cells, as taught inter alia by Yamanaka et al. 2006 (Cell 126: 663-676), Yamanaka et al. 2007 (Cell 131: 861-872) and Lin et al. 2009 (Nature Methods 6: 805-808).

Preferred cells as intended herein such as procoagulant cells as intended herein may include mesenchymal stem cells. The term "mesenchymal stem cell" or "MSC" as used herein refers to an adult, mesoderm-derived stem cell that is capable of generating cells of mesenchymal lineages, typically cells of three or more mesenchymal lineages, e.g., osteocytic (bone), chondrocytic (cartilage), myocytic (muscle), tendonocytic (tendon), fibroblastic (connective tissue), adipocytic (fat), stromogenic (marrow stroma) lineage. Commonly, but without limitation, a cell may be considered MSC if it is capable of forming cells of each of the adipocytic, chondrocytic and osteocytic lineages, using standard, art-accepted differentiation conditions and cellular phenotype evaluation methods, e.g., as described in Pittenger et al. 1999 (Science 284: 143-7) or Barberi et al. (PLoS Med 2: e161, 2005). MSC cells may be isolated from, e.g., bone marrow, blood, umbilical cord, placenta, foetal yolk sac, dermis especially foetal and adolescent skin (Young et al. 2001. Anat Rec 264: 51-62), periosteum, and adipose tissue (Zuk et al. 2001. Tissue Eng 7: 211-28). Human MSC, their isolation, in vitro expansion, and differentiation, have been described in, e.g., Pittenger et al. 1999 (supra), U.S. Pat. No. 5,486,359; U.S. Pat. No. 5,811,094; U.S. Pat. No. 5,736,396; U.S. Pat. No. 5,837,539; or U.S. Pat. No. 5,827,740.

The term also encompasses MSC obtained from bone marrow, which are commonly referred to as "bone marrow mesenchymal stem cells", "bone marrow stromal cells" or "BMSC". A sample of bone marrow for isolation of BMSC may be acquired, e.g., from iliac crest, femora, tibiae, spine, rib or other medullar spaces. In a preferred embodiment MSC or MSC populations as used herein may originate from bone marrow, e.g., may be isolated and optionally expanded from a bone marrow sample. MSC and MSC populations originated from bone-marrow can have characteristics (e.g., marker profile, function, expansion, differentiation, etc.) different from and/or favourable over MSC originated from other tissues, such as without limitation may more efficiently and/or more controllably differentiate into certain cell lineages. The terms MSC and BMSC also encompass the progeny of MSC or BMSC, e.g., progeny obtained by in vitro or ex vivo propagation of MSC or BMSC obtained from a biological sample of a subject.

Other cells as intended herein such as procoagulant cells as intended herein may include without limitation adult progenitor or stem cells obtained or derived from (e.g., removed or isolated from) tissues including muscle tissue (e.g., satellite cells), endocrine tissue (e.g., pancreas, gonads, adrenal gland, pineal gland, pituitary gland, thyroid and parathyroid glands), nervous tissue (e.g., neuronal or glial tissue), blood and immune system tissues, epithelial, liver, bone, cartilage, adipose or endothelial tissues.

Particularly preferred cells as described herein such as particularly cells having procoagulant activity are adult liver-derived progenitor or stem cells, more specifically such cells as detailed in the summary section.

As used herein, adult liver-derived progenitor or stem cells or adult liver progenitor cells or similar may generally denote liver-originating cells having progenitor or stem cell characteristics and capable of differentiating towards one or more liver cell types, such as for example capable of at least or only hepatic differentiation (i.e., differentiating towards hepatocytes or hepatocyte-like cells).

Cells as intended herein such as procoagulant cells which are partly or fully differentiated or mature, such as terminally differentiated cells (i.e., fully specialised cells that may be post-mitotic), may include without limitation muscle cells (e.g., cardiomyocytes, myocytes, myotubes, myoblasts, vascular smooth muscle cells), pancreatic endocrine cells (e.g., beta cells, alpha cells, delta cells, PP-producing cells or epsilon cells), nervous cells (e.g., neurons, glial cells such as astrocytes, oligodendrocytes, Schwann cells), cells of blood and immune systems (e.g., B- or T-lymphocytes, dendritic cells, granulocytes, macrophages, etc.), epithelial cells (e.g., keratinocytes, melanocytes, kidney cells, lung cells), liver cells (e.g., hepatocytes, oval cells), bone cells (osteoblasts, osteocytes, odontoblasts), chondrocytes, adipocytes, endothelial cells (e.g., vascular smooth muscle cells). Also intended are fused cells, e.g., cell hybrids.

As used herein, the term "antithrombin activator" refers to an agent (e.g., a compound, substance or molecule) which directly activates antithrombin. As such, an antithrombin activator increases the catalytic (antagonistic) activity (i.e., increased rate constant) of antithrombin towards its target(s), such as for example thrombin, factor Xa and/or factor IXa. Particularly preferably, an antithrombin activator increases the catalytic (antagonistic) activity of antithrombin towards at least factor Xa. In another preferred embodiment, an antithrombin activator may increase the catalytic (antagonistic) activity of antithrombin specifically towards factor Xa, such as for example but without limitation fondaparinux. Antithrombin activation by an antithrombin activator may be accomplished by any means, for example, and without limitation, by direct binding and induction of conformational changes in antithrombin, leading to increased accessibility and/or activity of the catalytic (target-binding) site. As used herein "antithrombin" refers to any of the known antithrombins, preferably antithrombin III (gene symbol SERPINC1). Accordingly, as used herein, "antithrombin activator" preferably refers to an activator of antithrombin III.

In an embodiment, the antithrombin activator according to the invention is heparin. In another embodiment, the antithrombin activator according to the invention is selected from the group consisting of unfractionated heparin and low molecular weight heparin. In a further embodiment, the antithrombin activator according to the invention is fondaparinux, that may be represented as 2-deoxy-6-O-sulfo-2-(sulfoamino)-α-D-glucopyranosyl-(1→4)-O-β-D-glucopyranuronosyl-(1→4)-O-2-deoxy-3,6-di-O-sulfo-2-(sulfoamino)-α-D-glucopyranosyl-(1→4)-O-2-O-sulfo-α-L-idopyranouronosyl-(1→4)-O-methyl-2-deoxy-6-O-sulfo-2-(sulfoamino)-α-D-glucopyranoside, decasodium salt. In a preferred embodiment, the antithrombin activator according to the invention is unfractionated heparin. As used herein, "unfractionated heparin" particularly refers to natural heparin, which is polydisperse consisting of molecular chains of varying length (usually ranging between about 5 and about 40 kDa). As intended herein, any type of heparin may be used. Typically, pharmaceutical grade heparin is derived from mucosal tissues of slaughtered meat animals such as porcine intestine or bovine lung. As used herein, "low molecular weight heparin" (LMWH) refers to heparin having typically an average molecular weight of less than about 8 kDa and for which at least about 60% of all chains have a molecular weight less than about 8 kDa. LMWH is obtained by various methods of fractionation or depolymerisation of polymeric heparin. Examples of LMWH include, without limitation, ardeparin, certoparin, enoxaparin, parnaparin, tinzaparin, dalteparin, reviparin and nadroparin.

As contemplated by the inventors, certain antithrombin activators may act through increasing the catalytic (antagonistic) activity of antithrombin (specifically) towards factor Xa. Accordingly, in some aspects and embodiments, what is contemplated are combinations, compositions, kits, methods and uses as described herein that employ, as an alternative to the antithrombin activator or in addition to the antithrombin activator, a Factor Xa inhibitor, particularly a Factor Xa inhibitor other than an antithrombin activator. Such Factor Xa inhibitor may be indirect or alternatively a direct Factor Xa inhibitor. Indirect Factor Xa inhibitors include for instance substances that inhibit the conversion of Factor X into Factor Xa. A direct Factor Xa inhibitor may act directly upon Factor Xa in the coagulation cascade, without using antithrombin as a mediator, thereby preventing Factor Xa mediated conversion of prothrombin into thrombin. By means of example, and without limitation, direct Factor Xa inhibitors include Apixaban, Edoxaban, Otamixaban, Rivaroxaban, DX9065a and YM466.

As used herein, the term "thrombin inhibitor" refers to a compound which directly binds to and inactivates thrombin. As such, a thrombin inhibitor significantly decreases or ideally completely or substantially completely blocks the catalytic activity of thrombin as conveniently measured by a decreased rate constant for its catalytic target(s), most notably fibrinogen. Thrombin inhibition by a thrombin inhibitor may be reversible or irreversible, preferably reversible. Thrombin inhibition by a thrombin inhibitor may be accomplished by any means, for example, and without limitation, by direct binding to the catalytic site of thrombin.

In an embodiment, the thrombin inhibitor according to the invention is selected from the group consisting of bivalirudin and hirudin. Chemically, bivalirudin (CAS No. 128270-60-0) is a synthetic congener of the naturally occurring drug hirudin. Naturally occurring hirudin typically contains a mixture of various isoforms of this protein. Hence, the term "hirudin" as used in herein particularly includes any protein having the primary amino acid sequence of a naturally occurring hirudin isoform, such as inter alia HV1, HV2, HV3, P1 or P2. Recombinant hirudin can be made to produce homogeneous preparations of hirudin such as for example, and without limitation, lepirudin and desirudin. Hirudin as intended herein also encompasses suitable derivatives or analogues of hirudin, e.g., by way of amino acid substitution, deletion, insertion, extension, functionalisation or chemical modification, said derivative having thrombin inhibitor activity; and further encompasses hybrids of more than one hirudin, which may be produced by genetic engineering. For example, WO 91/17250 describes a hirudin composed of the first 46 residues of HV1 followed by amino acids 47 to 65 of HV2.

In a preferred embodiment, the thrombin inhibitor is bivalirudin (for instance manufactured by The Medicines Company as Angiomax® or Angiox®). Whereas (natural or recombinant) hirudin and hirudin derivatives as well as bivalirudin are known to a skilled person, for further guidance consult inter alia Fenton et al. Semin Thromb Hemost., 1998, vol. 24, 87-91.

Particularly preferred combinations or compositions embodying the principles of the invention may comprise, consist essentially of or consist of an anti-thrombin activator selected from the group consisting of heparin, unfractionated heparin, low molecular weight heparin and fondaparinux, preferably unfractionated heparin, a thrombin inhibitor selected from the group consisting of bivalirudin and hirudin, preferably bivalirudin, and optionally cells selected from the group consisting of adult liver progenitor cells, mesenchymal stem cells (preferably bone marrow mesenchymal stem cells), skin fibroblasts, or liver myofibroblasts, preferably adult liver progenitor cells or liver myofibroblasts, most preferably adult liver progenitor cells.

Further particularly preferred combinations or compositions embodying the principles of the invention are disclosed in Table 1, i.e., combinations or compositions comprising, consisting essentially of, or consisting of substance 1, substance 2, and optionally cells.

TABLE 1

| substance 1 | substance 2 | cells |
|---|---|---|
| heparin | hirudin | |
| heparin | bivalirudin | |
| unfractionated heparin | hirudin | |
| unfractionated heparin | bivalirudin | |
| LMWH[1] | hirudin | |
| LMWH[1] | bivalirudin | |
| fondaparinux | hirudin | |
| fondaparinux | bivalirudin | |
| heparin | hirudin | procoagulant cells |
| heparin | bivalirudin | procoagulant cells |
| unfractionated heparin | hirudin | procoagulant cells |
| unfractionated heparin | bivalirudin | procoagulant cells |
| LMWH[1] | hirudin | procoagulant cells |
| LMWH[1] | bivalirudin | procoagulant cells |

TABLE 1-continued

| substance 1 | substance 2 | cells |
|---|---|---|
| fondaparinux | hirudin | procoagulant cells |
| fondaparinux | bivalirudin | procoagulant cells |
| heparin | hirudin | adult liver progenitor cells |
| heparin | bivalirudin | adult liver progenitor cells |
| unfractionated heparin | hirudin | adult liver progenitor cells |
| unfractionated heparin | bivalirudin | adult liver progenitor cells |
| LMWH[1] | hirudin | adult liver progenitor cells |
| LMWH[1] | bivalirudin | adult liver progenitor cells |
| fondaparinux | hirudin | adult liver progenitor cells |
| fondaparinux | bivalirudin | adult liver progenitor cells |
| heparin | hirudin | (bone marrow) mesenchymal stem cells |
| heparin | bivalirudin | (bone marrow) mesenchymal stem cells |
| unfractionated heparin | hirudin | (bone marrow) mesenchymal stem cells |
| unfractionated heparin | bivalirudin | (bone marrow) mesenchymal stem cells |
| LMWH[1] | hirudin | (bone marrow) mesenchymal stem cells |
| LMWH[1] | bivalirudin | (bone marrow) mesenchymal stem cells |
| fondaparinux | hirudin | (bone marrow) mesenchymal stem cells |
| fondaparinux | bivalirudin | (bone marrow) mesenchymal stem cells |
| heparin | hirudin | skin fibroblasts |
| heparin | bivalirudin | skin fibroblasts |
| unfractionated heparin | hirudin | skin fibroblasts |
| unfractionated heparin | bivalirudin | skin fibroblasts |
| LMWH[1] | hirudin | skin fibroblasts |
| LMWH[1] | bivalirudin | skin fibroblasts |
| fondaparinux | hirudin | skin fibroblasts |
| fondaparinux | bivalirudin | skin fibroblasts |
| heparin | hirudin | liver myofibroblasts |
| heparin | bivalirudin | liver myofibroblasts |
| unfractionated heparin | hirudin | liver myofibroblasts |
| unfractionated heparin | bivalirudin | liver myofibroblasts |
| LMWH[1] | hirudin | liver myofibroblasts |
| LMWH[1] | bivalirudin | liver myofibroblasts |
| fondaparinux | hirudin | liver myofibroblasts |
| fondaparinux | bivalirudin | liver myofibroblasts |

[1]LMWH includes ardeparin, certoparin, enoxaparin, parnaparin, tinzaparin, dalteparin, reviparin and nadroparin; preferably LMWH is enoxaparin.

The term "cell transplantation" carries its normal meaning and particularly refers to the administration of cells to a subject. The term "cell transplantation" can be used interchangeably with "cell therapy". Cell transplantation may be performed by any technique known in the art. By means of example, and without limitation, cells may be transplanted by infusion into a subject. Typically, cell infusion may be performed parenterally, e.g., intravascularly, subcutaneously, intradermally, or intramuscularly, preferably intravascularly. Cells may be administered for instance, and without limitation, systemically, topically or at the site of a lesion. It may be clear that, depending on the specific application, targeted tissues, therapeutic purpose or cell type, adjustment may be made accordingly in respect of routes of administration, as well as formulations, concentrations, etc.

As used herein, the term "thrombotic complications" or "procoagulant complications" may particularly refer to deleterious effects or complications associated with transplantation of cells having procoagulant activity, apart from clot formation per se. Such effects can be for instance, and without limitation, cell loss, cell rejection or inflammation. By cell loss or cell rejection is meant loss or rejection of transplanted cells. The result of these effects is a decrease of cell transplantation efficiency or cell engraftment potential, as less than, or in extreme cases none of, the administered total amount of cells is available to perform their intended function after transplantation. Cell loss can for instance occur due to inclusion of transplanted cells in clots. Cell rejection can for instance occur due to an immunological response of the host. An inflammatory response can for instance be associated, or result from, the activation of the coagulation cascade. Alternatively, or in addition hereto, inflammation can be associated with, result from, or cause cell rejection.

Also provided are compositions comprising the herein taught combinations and further comprising one or more other components. For example, components may be included that can maintain or enhance the viability of cells. By means of example and without limitation, such components may include salts to ensure substantially isotonic conditions, pH stabilisers such as buffer system(s) (e.g., to ensure substantially neutral pH, such as phosphate or carbonate buffer system), carrier proteins such as for example albumin, media including basal media and/or media supplements, serum or plasma, nutrients, carbohydrate sources, preservatives, stabilisers, anti-oxidants or other materials well known to those skilled in the art. Also disclosed are methods of producing said compositions by admixing the respective components of the herein taught combinations with said one or more additional components as above. The compositions may be for example liquid or may be semi-solid or solid (e.g., may be frozen compositions or may exist as gel or may exist on solid support or scaffold, etc.). Cryopreservatives such as inter alia DMSO are well known in the art.

As noted elsewhere, pharmaceutical compositions as taught herein comprise one or more pharmaceutically acceptable excipient.

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, anti-oxidants, tonicity controlling agents, absorption delaying agents, and the like. The use of such media and agents for pharmaceutical active substances is well known in the art. Such materials should be non-toxic and should not interfere with the activity of the cells.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of its environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregeletanized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants. For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating said support with a liquid suspension containing said cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell populations can be administered in a manner that permits them to survive, grow, propagate and/or differentiate towards desired cell types such as, e.g., hepatocytes. The cells or cell populations may be grafted to or may migrate to and engraft within the intended organ, such as, e.g., liver. Engraftment of the cells or cell populations in other places, tissues or organs such as liver, spleen, pancreas, kidney capsule, peritoneum or omentum may be envisaged.

In an embodiment the pharmaceutical cell preparation as defined above may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the desired cells. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

The present combinations, pharmaceutical compositions and other related aspects are particularly useful for transplantation of cells as described herein such as particularly procoagulant cells, even more particularly for the treatment of diseases or conditions which can benefit from transplantation of said cells in subjects.

Except when noted, "subject" or "patient" are used interchangeably and refer to animals, preferably vertebrates, more preferably mammals, and specifically includes human patients and non-human mammals. Accordingly, "subject" or "patient" as used herein means any animal, mammalian or human patient or subject to which the combinations or compositions as taught herein can be administered. Preferred patients are human subjects.

As used herein, the terms "treat" or "treatment" refer to both therapeutic treatment and prophylactic or preventative measures, wherein the object is to prevent or slow down (lessen) an undesired physiological change or disorder. Beneficial or desired clinical results include, but are not limited to, alleviation of symptoms, diminishment of extent of disease, stabilised (i.e., not worsening) state of disease, delay or slowing of disease progression and occurrence of complications, amelioration or palliation of the disease state. "Treatment" can also mean prolonging survival as compared to expected survival if not receiving treatment.

As used herein, a phrase such as "a subject in need of treatment" includes subjects, such as mammalian or human subjects, that would benefit from treatment of a given condition, preferably a condition or disease as above. Such subjects will typically include, without limitation, those that have been diagnosed with the condition, those prone to have or develop the said condition and/or those in whom the condition is to be prevented.

The combinations and pharmaceutical compositions described herein may be used alone or in combination with any of the known therapies or active compounds for the respective disorders. The administration may be simultaneous or sequential in any order.

If the cells are derived from heterologous (i.e., non-autologous) source, concomitant immunosuppression therapy may be typically administered, e.g., using immunosuppressive agents, such as cyclosporine or tacrolimus (FK506).

By means of example and not limitation, where the combinations or pharmaceutical compositions as intended herein contain liver cells, such as liver progenitor or stem cells (e.g., ADHLSC cells) or hepatocytes, they may be employed inter alia for the treatment of liver-associated diseases including but not limited to liver dysfunction or failure, hepatitis and inborn errors of metabolism.

Non exhaustive examples of inborn metabolic deficiencies of liver include phenylketonuria and other aminoacidopathies, haemophilia and other clotting factor deficiencies, familial hypercholesterolemia and other lipid metabolism disorders, urea cycle disorders, glycogenosis, galactosemia, fructosemia, tyrosinemia, protein and carbohydrate metabolism deficiencies, organic aciduria, mitochondrial diseases, peroxysomal and lysosomal disorders, protein synthesis abnormalities, defects of liver cell transporters, defect of glycosylation and the like.

Further liver-associated diseases or conditions include, without limitation, acquired progressive liver degenerative diseases, fulminant liver failure and acute or chronic liver failure, human hepatotropic virus infections (HBV, HAV, HCV, HEV, HDV, . . . ).

Other disease states or deficiencies typified by loss of liver mass and/or function, and that could benefit from combinations or pharmaceutical composition comprising liver cells as described herein include but are not limited to Alagille syndrome, alcoholic liver disease (alcohol-induced cirrhosis), a1-antitrypsin deficiency (all phenotypes), hyperlipidemias and other lipid metabolism disorders, autoimmune hepatitis, Budd-Chiari syndrome, biliary atresia, progressive familial cholestasis type I, II and III, cancer of the liver, Caroli Disease, Crigler-Najjar syndrome, fructosemia, galactosemia, carbohydrate deficient glycosylation defects, other carbohydrate metabolism disorders, Refsum disease and other peroxysomal diseases, Niemann Pick disease, Wolman disease and other lysosomal disorders, tyrosinemia, triple H, and other amino acid metabolic disorders, Dubin-Johnson syndrome, fatty liver (non alcoholi steato hepatitis), Gilbert Syndrome, Glycogen Storage Disease I and III, hemochromatosis, hepatitis A-G, porphyria, primary biliary cirrhosis, sclerosing cholangitis, tyrosinemia, clotting factor deficiencies, hemophilia B, phenylketonuria, Wilson's Disease, fulminant liver failure, post hepatectomy liver failure, mitochondrial respiratory chain diseases.

By means of example and not limitation, combinations or pharmaceutical compositions, particularly those comprising liver cells, may be advantageously administered via injection (encompassing also catheter administration) or implantation, e.g. localised injection, systemic injection, intrasplenic injection (see also Gupta et al., Seminars in Liver Disease 12: 321, 1992), injection to a portal vein, injection to liver pulp, e.g., beneath the liver capsule, parenteral administration, or intrauterine injection into an embryo or foetus. For example, the combinations or pharmaceutical compositions comprising liver cells or liver derived cells as described herein may be used for tissue engineering and cell therapy via liver cell transplantation (LCT). Liver cell transplantation, and liver stem cell transplantation (LSCT) refers to the technique of infusing mature hepatocytes or liver progenitor cells in any way leading to hepatic access and engraftment of the cells, preferably via the portal vein, but also by direct hepatic injection, or by intrasplenic injection. In another example, the combinations or pharmaceutical compositions comprising the mesenchymal stem cells as described herein may be used for any solid organ repair (brain, heart, liver, kidney, pancreas, spleen, lung, gut, bladder, gallbladder), to control immune disorder, to control Cröhn disease and other auto-immune diseases, to control graft versus host disease, to control organ rejection following transplantation, In another example, the combinations or pharmaceutical compositions comprising the skin fibroblasts as described herein may be used for skin repair or bone matrix formation. In a further example, the combinations or pharmaceutical compositions comprising the liver myofibrobasts as described herein may be used for treating or repairing damage from connective tissue disease or for creating scaffolds in combination with other cells.

In current human studies of autologous mononuclear bone marrow cells, empirical doses ranging from 1 to $4\times10^7$ cells have been used with encouraging results. However, different scenarios may require optimisation of the amount of administered cells. Thus, the quantity of cells to be administered will vary for the subject being treated. In a preferred embodiment, between $10^2$ to $10^{10}$ or between $10^2$ to $10^9$, or between $10^3$ to $10^{10}$ or between $10^3$ to $10^9$, or between $10^4$ to $10^{10}$ or between $10^4$ to $10^9$, such as between $10^4$ and $10^8$, or between $10^5$ and $10^7$, e.g., about $1\times10^5$, about $5\times10^5$, about $1\times10^6$, about $5\times10^6$, about $1\times10^7$, about $5\times10^7$, about $1\times10^8$, about $5\times10^8$, about $1\times10^9$, about $2\times10^9$, about $3\times10^9$, about $4\times10^9$, about $5\times10^9$, about $6\times10^9$, about $7\times10^9$, about $8\times10^9$, about $9\times10^9$ or about $1\times10^{16}$ cells can be administered to a human subject. In further embodiments, between $10^6$ to $10^8$ cells per kg body weight or between $1\times10^7$ to $9\times10^7$ cells per kg body weight, e.g., about $1\times10^7$, about $2\times10^7$, about $3\times10^7$, about $4\times10^7$, about $5\times10^7$, about $6\times10^7$, about $7\times10^7$, about $8\times10^7$, about $9\times10^7$ or about $1\times10^8$ cells per kg body weight can be administered to a human subject. For example, such number of cells or such number of cells per kg body weight may particularly refer to the total number of cells to be administered to a subject, which administration may be suitably distributed over one or more doses (e.g., distributed over 2, 3, 4, 5, 6, 7, 8 9 or 10 or more doses) administered over one or more days (e.g., over 1, 2, 3, 4 or 5 or more days). However, the precise determination of a therapeutically effective dose may be based on factors individual to each patient, including their size, age, size tissue damage, and amount of time since the damage occurred, and can be readily ascertained by those skilled in the art from this disclosure and the knowledge in the art.

Suitably, in a composition to be administered, cells may be present at a concentration between about $10^4$/ml to about $10^8$/ml, preferably between about $10^5$/ml and about $10^7$/ml, yet more preferably between about $1\times10^6$/ml and about $1\times10^7$/ml, such as, e.g., about $5\times10^6$/ml.

The dosage or amount of active substances as disclosed herein used (e.g., antithrombin activator, thrombin inhibitor), optionally in combination with one or more other pharmaceutically or biologically active ingredients as defined above, depends on the individual case and is, as is customary, to be adapted to the individual circumstances to achieve an optimum effect. Thus, it depends on the nature and the severity of the disorder to be treated, and also on the sex, age, body weight, diet, general health, individual responsiveness of the human or animal to be treated, on the efficacy, metabolic stability and duration of action of the compounds used, on mode and time of administration, rate of excretion, on whether the therapy is acute or chronic or prophylactic, or on whether other pharmaceutically or biologically active ingredients are administered, or other therapies applied, in addition to the active substance(s) of the invention.

Without limitation, a typical single dosage might range from about 1 µg/kg to about 250 mg/kg body weight or more, preferably from about 1 µg/kg to about 100 mg/kg body weight, more preferably from about 0.01 mg/kg to about 50 mg/kg body weight, even more preferably from about 0.01 mg/kg to about 10 mg/kg body weight, and still more preferably from about 0.05 mg/kg to about 10 mg/kg body weight or from about 0.05 mg/kg to about 1 mg/kg body weight, depending on the factors mentioned above.

For repeated administrations over several days or longer, the treatment is sustained until a desired suppression of disease symptoms occurs. A preferred dosage of the agent may be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered as a single daily dose, divided over one or more daily doses, or essentially continuously, e.g., using a drip infusion, or intermittently, e.g., every week or every three weeks.

In embodiments, the antithrombin activator and particularly unfractionated heparin may be administered to a subject via a cell suspension typically comprising about 5-15 Ul/ml, more typically about 8-12 Ul/ml, and even more typically about 10 Ul/ml. When intravenous administration of antithrombin activator and particularly unfractionated heparin is indicated, typical dose may be about 10-30 Ul/kg/hr, more typically about 15-25 Ul/kg/hr, and even more typically about 20 Ul/kg/hr. Understandably, dose may be adapted according to coagulation tests.

Preferably, the thrombin inhibitor may be administered to a subject at between about 0.05 and about 5 mg/kg body weight, more preferably between about 0.1 and about 3 mg/kg body weight, even more preferably between about 0.2 and about 2 mg/kg body weight; more preferably for bivalirudin between about 0.50 and about 3.00 mg/kg body weight, and yet more preferably between about 0.50 and about 2 mg/kg body weight, and even more preferably between about 0.75 and about 1.75 mg/kg body weight, or also preferably between about 1.75 and about 3.00 mg/kg body weight or more preferably between about 2.25 and about 2.75 mg/kg body weight, such as for example about 2.50 mg/kg body weight; and more preferably for hirudin between about 0.2 and about 0.6 mg/kg body weight, and yet more preferably between about 0.3 and about 0.5 mg/kg body weight, and even more preferably at about 0.4 mg/kg body weight.

The invention will now be illustrated by means of the following examples, which do not limit the scope of the invention in any way.

EXAMPLE 1

Materials and Methods

Cell Preparations

Adult-derived human liver mesenchymal stem cells (ALDSC, ADHLSC) were obtained from healthy liver donors as previously described (Najimi et al. Cell Transplant., 2007, vol. 16: 717-28). Cells were suspended in an albumin solution containing or not heparin at a concentration of 10 U/ml (or more when specified). As a control cryopreserved/thawed human hepatocytes were used. Liver isolation and hepatocyte cryopreservation/thawing procedures were previously published in detail (Sokal et al. Transplantation, 2003, vol. 76, 735-738). Human fibroblasts were collected by skin biopsy (medio-anterior side of the forearm) of 8 years old to 35 years old volunteers after written informed consent as previously described (Lysy et al. Hepatology, 2007, vol. 46, 1574-1585). Bone marrow samples were collected by aspiration of vertebrae or iliac crests of postmortem donors aged 8 to 67 years. Aspirates were collected into heparinized syringes containing 10% Hanks' balanced salt solution (Invitrogen, Merelbeke, Belgium) and were processed within 48 h according to a previously described protocol (Lysy et al. Cell Prolif., 2008, vol. 41, 36-58).

Tissue Factor Expression of Adult-derived Human Liver Mesenchymal Stem Cells Suspension Presence of the classical membrane-bound TF form and of the TFPI were analyzed by reverse-transcription polymerase chain reaction (RT-PCR). Messenger ribonucleic acid (mRNA) was extracted from $0.5 \times 10^6$ cells using the Tripure isolation reagent kit (Roche Applied Science, Brussels, Belgium) following the manufacturer's instructions. One-step RT-PCR was performed on a Thermocycler instrument (Applied Biosystems, Lennik, Belgium) with primers synthesized at Invitrogen. RT-PCR for TF or glyceraldehyde 3-phosphate dehydrogenase (GAPDH) was realized with the primers detailed in Table 2.

TABLE 2

| Primer | Sequence | SEQ ID NO |
|---|---|---|
| TF sense primer | 5-TGAATGTGACCGTAGAAGATGA-3 | 1 |
| TF antisense primer | 5-GGAGTTCTCCTTCCAGCTCT-3 | 2 |
| TFPI sense primer | 5-GGAAGAAGATCCTGGAATATCGAGG-3 | 3 |
| TFPI antisense primer | 5-CTTGGTTGATTGCGGAGTCAGGGAG-3 | 4 |
| GAPDH sense primer | 5-CGGACTCAACGGATTTGGTCGTAT-3 | 5 |
| GAPDH antisense primer | 5-AGCCTTCTCCATGGTGGT-3 | 6 |
| As-TF sense primer | 5-TCTTCAAGTTCAGGAAAGAAATATTCT-3 | 7 |
| As-TF antisense primer | 5-CCAGGATGATGACAAGGATGA-3 | 8 |

Products were separated by electrophoresis on 1% agarose gel and visualized with ethidium bromide under ultraviolet lamp.

A real-time RT-PCR for TF, as-TF, TFPI, and cyclophilin A was also realized on a StepOnePlus real-time PCR system (Applied Biosystems, California, USA) using TaqMan® Gene Expression Assays, listed in Table 3. For the TF expression, two assays were used, one (TF common) amplifying a region present in both membrane and soluble (alternative splicing, asTF) form, and the other (TF membrane) amplifying a region present only in the membrane (classical) form. The parameter Ct was derived for each cDNA sample and primer pair and the Cyclophilin A Ct was subtracted to obtain the ΔCt. Then the ΔΔCt was obtained by subtracting the calibrator gene Ct, and the results expressed as fold change of the mRNA amount (FIG. 9). The asTF expression was calculated as difference between the ΔΔCt of the TF common and TF membrane. Then the Primers (obtained from Applied Biosystems) were as detailed in Table 3.

TABLE 3

| Gene | Reference TaqMan® Gene Expression Assays | Amplicon length |
|---|---|---|
| TF common | Hs01076032_m1 | 69 |
| TF membrane | Hs01076029_m1 | 85 |

TABLE 3-continued

| Gene | Reference TaqMan ® Gene Expression Assays | Amplicon length |
|---|---|---|
| TFPI | Hs01041344_m1 | 78 |
| Cyclophilin A | Hs99999904_m1 | 98 |

Pro-coagulant Activity of Adult-derived Human Liver Mesenchymal Stem Cells Suspension Measurements were performed on a ROTEM® delta analyser (Pentapharm, Munich, Germany). ROTEM assesses the kinetics and quality of clot formation and clot lysis in real-time. The clotting time (CT) is defined as the period of time from the start of the analysis until the start of clot formation, normally until the 2 mm amplitude is reached. The clot formation time is defined as the period until the 20 mm amplitude is reached. The alpha angle is defined as the angle between the centre line and a tangent to the curve through the 2 mm amplitude point, which is the end of the CT. The maximum amplitude of the curve is defined as the maximum clot firmness. The maximum of lysis represents the maximum fibrinolysis detected during the measurement.

Briefly, after a short rest period, 300 µl of whole blood was pipetted into a cup pre-warmed at 37° C. Suspended cells were subsequently added to whole blood ($5 \times 10^5$ cells if no specification). 20 µl of trigger reagent containing tissue factor (Innovin, Siemens, Marburg, Germany. Final dilution 1:17000/0.35 pM) diluted in Owren buffer (Siemens, Marburg, Germany) was then added, when specified, to the cell-blood mixture followed by necessary addition of 20 µl of 0.2 M $CaCl_2$. After calcium addition, measurements started automatically. For plasma assays, cells ($5 \times 10^5$ cells if no specification) were incubated in 3.8 ml of citrated blood at 37° C. for 30 minutes. After incubation, whole blood was centrifuged at 4500 rpm for 10 minutes. 300 µl of the obtained plasma was then ready for the protocol, pipetted into the cup followed by addition or not of tissue factor and $CaCl_2$.

Statistics

Statistically significant (*P<0.05, P<0.01, *P<0.001) differences were assessed by Mann-Whitney tests. Kruskal-Wallis test was applied for one way ANOVA analysis.

EXAMPLE 2

Procoagulant Activity of Adult-derived Human Liver Mesenchymal Stem Cells

Procoagulant activity of adult-derived human liver mesenchymal stem cells (ALDSC, ADHLSC) was demonstrated by a thromboelastometry method. This procoagulant activity is more important than that of the mature hepatocytes as evaluated by clotting time in the thromboelastograph test (FIG. 1). Furthermore, and conversely to hepatocyte procoagulant activity, it is shown that the ALDSC procoagulant activity is not fully inhibited by unfractionated heparin, low molecular weight heparin (data not shown), anti-vitamin K drugs (data not shown) or anti-thrombin drugs used alone (hirudin, bivalirudin) (FIGS. 2-3). We found that the concomitant use of unfractionated heparin and hirudin or bivalirudin is an original specific and synergistic combination allowing to modulate the pro-coagulant activity of adult-derived human liver mesenchymal stem cells (FIGS. 4-5). We also demonstrated a procoagulant activity of fibroblasts, bone marrow mesenchymal stem cells, but not for bone marrow haematopoietic stem cells (FIGS. 6-7). Using analogous experiments, concomitant use of unfractionated heparin and hirudin or bivalirudin is also shown to modulate the pro-coagulant activity of fibroblasts and bone marrow mesenchymal stem cells.

EXAMPLE 3

Adult-derived Human Liver Mesenchymal Stem Cells Express TF

The expression of TF and its natural inhibitor TFPI at the mRNA level using RT-PCR was assayed (FIG. 8). Both the membrane form and the alternatively-spliced variant of TF mRNA (as-TF) were expressed in adult-derived human liver mesenchymal stem cells (ALDSC). In additional experiments, real-time RT-PCR was used to quantify TF, as-TF, TFPI mRNA levels as shown in FIG. 9.

EXAMPLE 4

Cell Transplantation

ALDSC are suspended at a concentration of $5 \times 10^6$ cells/ml in a solution of Hibumin (5%), containing bicarbonate (0.84 g/l), glucose (2.5 g/l) and unfractionated heparin (10 Ul/ml). The ALDSC suspension is parenterally infused in a subject. During cell infusion, the subject receives bivalirudin (1.75 mg/kg). Between consecutive cell infusions, the subject receives bivalirudin (0.25 mg/kg) for 2 to 4 hours, depending on the thromboelastometry test.

It is clear that concomitant administration of an antithrombin activator (e.g. heparin) and a thrombin inhibitor (e.g. bivalirudin) upon cell transplantation improves cell transplantation efficiency and cell engraftment potential. Concomitant administration of an antithrombin activator and a thrombin inhibitor upon cell transplantation reduces the procoagulant activity of the cells and prevents cell transplantation-associated thrombosis as well as cell transplantation-associated complications such as cell loss, cell rejection and inflammation.

EXAMPLE 5

Combination of Bivalirudin and Heparin Prevents Risk of Human Liver Progenitor Cells Induced Thrombosis Methods The protocol, including all experiments on human samples, and the human off label anticoagulant protocol use, and the informed consents were approved by the institution ethical review board.

Cell Preparations hALPC cells were obtained from healthy liver donors (n=6, aged 9 to 44 years) as previously described (Najimi et al., Cell Transplant. 2007; 16:717-728). Cells were studied freshly trypsinised or after cryopreservation/thawing at passages 4 to 6. Cells were suspended in an albumin solution containing or not containing heparin at a concentration of 10 U/mL (or more when specified). We also used, as a control, cryopreserved/thawed human hepatocytes (n=5, aged 16 to 44 years). Liver isolation and hepatocyte cryopreservation/thawing procedures were previously published in detail (Sokal et al., Transplantation. 2003; 76:735-738).

Bone marrow samples were collected by aspiration of vertebrae or iliac crests of 3 postmortem organ donors aged 8 to 67 years. Aspirates were collected into heparinised syringes containing 10% Hanks' balanced salt solution (Invitrogen, Merelbeke, Belgium) and were processed within 48 h according to a previously described protocol (Lysy et al., Cell Prolif. 2008; 41:36-58).

Human fibroblasts were collected by skin biopsy (medio-anterior side of the forearm) of 18-year-old to 35-year-old volunteers (n=3) after written informed consent as previously described (Lysy et al., Hepatology. 2007; 46:1574-1585).

Human liver non-parenchymal cells were obtained after liver isolation performed in our Tissue Bank, filtration and 2 low speed centrifugations of the cell suspension from three different donors (one neonate liver and two 12-years-old donors). Next, human stellate cells were isolated by Nicodenz (Myegaard, Oslo, Norway) gradient centrifugation according to established protocols (Guimarães et al., J Hepatol. 2010; 52(3):389-397). Activated myofibroblasts were obtained from the isolated stellate cells.

Blood

Blood was obtained from male donors aged 29 to 40 years (n=5).

Procoagulant Activity of hALPCs Suspension

Measurements were performed on a ROTEM® delta analyser (Pentapharm, Munich, Germany). ROTEM® assesses the kinetics and quality of clot formation and clot lysis in real-time. The clotting time (CT) is defined as the period of time from the start of the analysis until the start of clot formation, normally until the 2 mm amplitude is reached. The clot formation time is defined as the period until the 20 mm amplitude is reached. The alpha angle is defined as the angle between the centre line and a tangent to the curve through the 2 mm amplitude point, which is the end of the CT. The maximum amplitude of the curve is defined as the maximum clot firmness. The maximum of lysis represents the maximum fibrinolysis detected during the measurement. We focused on CT.

Briefly, after a short rest period, 300 µl of whole blood was pipetted into a cup pre-warmed at 37° C. Suspended cells were subsequently added to whole blood (5×10exp5 cells if no specification). Twenty µl of trigger reagent containing tissue factor (TF) (Innovin, Siemens, Marburg, Germany. Final dilution 1:17000/0.35 pM) diluted in Owren buffer (Siemens, Marburg, Germany) was then added to the cell-blood mixture followed by the necessary addition of 20 µl of 0.2 M CaCl2. After calcium addition, measurements started automatically. The procoagulant activity (PCA) of cells was also determined without addition of Innovin. To ascertain the role of TF in this coagulation model, cells were pre-incubated at room temperature for 10 minutes with either 0.2 mg/mL mAb anti-human TF IgG1 (American Diagnostica) or 0.2 mg/mL mAb mouse IgG1 (clone11711.11; RnD Systems, Abingdon, United Kingdom) before extensive washing in albumin 5% and thromboelastometry assay.

For plasma assays, cells (5×10exp5 cells if no specification) were incubated in 3.8 ml of citrated blood at 37° C. for 30 minutes. After incubation, whole blood was centrifuged at 4500 rpm for 10 minutes. Three hundred µl of the obtained plasma was then ready for the protocol, pipetted into the cup followed by addition or not of Innovin and CaCl2.

For plasma deficient assays, suspended cells (5×10exp5 cells if no specification) were added to 300 µl of plasma before addition of Innovin and CaCl2.

For modulation of PCA assays, cells were suspended in albumin 5% with or without non-fractionated heparin (Heparin Leo®, Leo) at a concentration of 10 Ul/ml. Enoxaparin (Clexane®, Aventis Pharma) at a concentration of 1 Ul/ml according to publications (Guimarães et al., J Hepatol. 2010; 52(3):389-397), fondaparinux (Arixtra®, GSK) at a concentration of 0.34 mg/l (clinical dose extrapolation 2.5 mg for adult weight and from publications (Feng et al., Clin Ther. 2009; 31:1559-1567), hirudin (Refludan®, Celgène Europe Limited) at a concentration of 5.7 µg/ml (clinical dose extrapolation 0.4 mg/kg), bivalirudin (Angiox®, The Medicines Company) at a concentration of 10.7 µg/ml (clinical dose extrapolation 0.75 mg/kg) were then added to blood or plasma. Dose extrapolation was based on circulating blood volume according to weight (70 ml/kg).

If no coagulation was observed after 1800 sec, thromboelastometry was arbitrary stopped.

Tubing Loop

A whole-blood experiment protocol was adapted from a model previously described (Johansson et al., Diabetes. 2005; 54:1755-1762). Loops made of polyvinylchloride tubing (inner diameter 6.3 mm, length 390 mm) and treated with a Corline heparin surface were purchased from Corline (Uppsala, Sweden). Loops were supplemented with cell samples (5×10exp5) suspended in phosphate buffered saline before blood addition. Five mL of non-anti-coagulated blood from healthy volunteers was then added to each loop. To generate a blood flow of about 45 mL/minute, loop devices were placed on a platform rocker inside a 37° C. incubator. Blood samples were collected into ethylene diamine tetraacetic acid (4.1 mmol/L final concentration) and citrate (12.9 mmol/L final concentration) tubes before and 30 minutes after start. Platelets were counted on a XE-2100 automate (Sysmex, Japan) and D-Dimers were evaluated by immunoturbidimetric assay (Innovance D-Dimer, Siemens, Marburg, Germany) on a CA-7000 (Sysmex, Japan).

Anti-Xa Activity Measurement

Anti-Xa activity measurement was performed using the Biophen Heparin (LRT) kit adapted on a CA7000 (Siemens, Marburg, Germany). Briefly, the assay is a chromogenic kinetics method based on the inhibition of a constant amount of factor Xa, by the tested heparin (or other anti-Xa substance) in presence of endogenous antithrombin, and hydrolysis of a factor Xa specific chromogenic substrate by the factor Xa in excess. After 30 min incubation of cells suspended in albumin supplemented or not with heparin (10 Ul/ml, 50 Ul/ml, and 100 Ul/ml) in blood, anti-Xa activity was measured in plasma obtained after blood centrifugation.

TF and TFPI Expression of hALPCs Suspension

Immunofluorescence studies were performed to evaluate the presence of TF. For this, human adult liver-derived stem cells were placed on cover slips and fixed by paraformaldehyde 4% (Merck, Darmstadt, Germany) for 20 minutes. Then, these cells were incubated with Triton X-100 (Sigma, Bornem, Belgium) 1% in Tris base sodium buffer (50 mmol/L Tris-HCl pH 7.4 and 150 mmol/L NaCl) (Organics [VWR], Leuven, Belgium) for 15 minutes and then with milk 3% in Tris base sodium buffer for 1 hour. The primary antibody, murine IgG1 monoclonal antibody (mAb) anti-TF (immunoglobulin [Ig]G1 n4508; American Diagnostica, Andresy, France) was diluted (1/50) in Tris base sodium and incubated with cells for 1 hour. The secondary antibody used was fluorescein isothiocyanate conjugated anti-mouse IgG (Sigma). The nuclei were revealed by 4-, 6-diamidino-2-phenylindole (DAPI; Sigma) staining. Negative experimental controls were performed (absence of primary or secondary antibodies). The presence of TF was also confirmed by flow cytometric analysis. In order to detect the membrane-bound form of TF, cells were washed in phosphate-buffered saline supplemented with 0.5% bovine serum albumin (FACS buffer) and incubated for 20 minutes at 4° C. with the fluorescein isothiocyanate (FITC)-conjugated IgG1 mAb against TF no. 4508CJ (American Diagnostica) or the corresponding isotype-matched control mAb (BD Biosciences, Erembogedem, Belgium) diluted in FACS buffer containing 10% decomplemented pooled human serum. To detect the cytosolic form of TF, cells were incubated with Cytofix/Cytoperm (BD Biosciences) for 20 mn at room temperature and washed with Permwash (BD Biosciences). The samples were then incubated for 20 minutes at room temperature with FITC-conjugated anti TF mAb or the corresponding isotype-matched control mAb (BD Biosciences) diluted in permwash. Cell fluorescence was measured using a BD FACS CANTO II flow cytometer and analysed using the BD FACS Diva software.

No anti-TFPI antibody was obtained to evaluate tissue factor pathway inhibitor (TFPI) expression by immunocytochemistry or flow cytometry analysis.

Presence of the 2 forms of TF and of TFPI was analyzed by reverse-transcription polymerase chain reaction (RT-PCR). Messenger ribonucleic acid (mRNA) was extracted from $0.5 \times 10exp6$ cells using the Tripure isolation reagent kit (Roche Applied Science, Brussels, Belgium) following the manufacturer's instructions. One-step RT-PCR was performed on a Thermocycler instrument (Applied Biosystems, Lennik, Belgium) with primers synthesized at Invitrogen. RT-PCR for TF or glyceraldehyde 3-phosphate dehydrogenase (GAPDH) was realized with the primers detailed in Table 2.

Products were separated by electrophoresis on 1% agarose gel and visualized with ethidium bromide under ultraviolet lamp.

A real-time RT-PCR for TF, as-TF, TFPI, and cyclophilin A was also realized on a StepOnePlus real-time PCR system (Applied Biosystems, California, USA) using TaqMan® Gene Expression Assays, listed in Table B. For the TF expression, two assays were used, one (TF common) amplifying a region present in both membrane and soluble (alternative splicing, as-TF) form, and the other (TF membrane) amplifying a region present only in the membrane (classical) form. The parameter Ct was derived for each cDNA sample and primer pair and the Cyclophilin A Ct was subtracted to obtain the ΔCt. Then the ΔΔCt was obtained by subtracting the calibrator gene Ct, and the results expressed as fold change of the mRNA amount. The as-TF expression was calculated as difference between the ΔΔCt of the TF common and TF membrane. The primers were as detailed in Table 3.

CAPAN cell line was used as TF positive control while HUVEC cell line as TFPI positive control.

Infusions of Patients and Anti-coagulation Protocol

A 3 years old girl, suffering from severe OTC deficiency (<1% activity), was the first hALPCs recipient. The diagnosis was established at 12 days post birth and confirmed by DNA analysis indicating a de novo mutation of exons 6 and 8 on the paternal allele of OTC gene.

She received 2 separate infusions of 30 million of hALPCs per kg body weight, from a male donor, with a 2 weeks interval between infusions. In total, the patient received 0.9 billion of progenitor cells. The cells were suspended in albumin 5% and heparin (10 UI/ml).

The first hALPCs infusion was performed under general anaesthesia without any pre-medication. A transcutaneous catheter was placed in the main portal vein branch under fluoroscopy and ultrasound guidance after the injection of one dose of Cefazolin (40 mg/kg). Cells infusion was performed using a syringe of 50 ml at a flow rate of 100 cc/h.

Immune suppression was administrated to the patient using tacrolimus (Prograft®, Astellas Pharma) monotherapy (0.1 mg/kg) corresponding to 2 mg per day in 2 divided doses to reach trough levels of 6-7 ng/ml. Prophylactic antibiotherapy with Cefazolin (40 mg/kg) 2 times post infusion with 8 hours interval between the 2 doses was administrated. The infusion and post infusion course were unremarkable and the child was discharged from the hospital on day 3 post-infusion.

The second hALPCs infusion was performed two weeks later. At that time, a partial thrombosis of an intra-hepatic portal vein branch occurred and led to arrest of infusion. This adverse event was treated by heparin and coumarinic anticoagulant (5 mg/day).

D-Dimer level was markedly elevated after both cell infusion courses. This adverse event was without consequence for the patient but justified to investigate further the procoagulant effect of the progenitor cells.

The second patient was a 24 years old man, with an intermediate type I/II Crigler-Najjar syndrome not responding to phenobarbital. The diagnosis was established at one month after birth and confirmed by DNA analysis indicating a mutation on the UDP-Glucuronosyltransferase 1A1 gene with presence of homozygous state of L443P mutation. The patient received a total of 2.2 billion hALPCs administered in 7 infusions over 2 days. Prior to the portal catheter placement, the patient received pre-medication including Cefazolin (1 gr). The catheter was under ultra-sound control placed in the portal system. Solumedrol (80 mg) was injected before infusion. The immune suppressive treatment consisted in tacrolimus (Prograft®, Astellas Pharma), targeting blood levels of 6-8 ng/ml. A specific coagulation prophylaxis was prescribed; cells were suspended in albumin 5% and heparin at a concentration of 10 Ul/ml. During cell infusion, the subject received bivalirudin (1.75 mg/kg). Between consecutive cell infusions, the subject received bivalirudin (0.25 mg/kg) for 2 to 4 hours, depending on the thromboelastometry test. Coagulation tests including thromboelastometry (CT), platelets count (normal values: 150-350 $10exp3/\mu l$) and D-Dimers levels (normal values: <500 ng/ml), Thrombin Time (TT, normal values: 15-24 sec), Prothrombin Time (PT, normal values: 9-14 sec) and Partial Thromboplastin time (PTT, normal values: 20-33 sec) were repetitively performed before, 20 min after beginning and at the end of each infusion. Liver Doppler ultra-sound was performed after each infusion to access portal flow.

The third patient was a 17 years old teenager suffering from Glycogenosis type 1a, documented by genetic analysis (G188R mutation and 380insC insertion) and absence of glucose-6 phosphatase activity on liver biopsy. He also received antibiotic prophylaxis prior to portal catheter placement and steroids before infusion. The same immune suppressive regime was applied. The patient received a total of 3 billion progenitor cells administered in 7 infusions over 3 days aiming to control recurrent hypoglycemia. The same anticoagulation protocol and coagulation including liver Doppler ultra-sound follow-up was applied.

Statistics

Statistically significant (*P<0.05, P<0.01, *P<0.001) differences were assessed by Mann-Whitney tests. The significant values were adjusted according Bonferroni correction to avoid type 1 error. Kruskal-Wallis test was applied for one way ANOVA analysis.

Results

Procoagulant Activity of hALPCs

Thromboelastometry Method and Tubing Loop

We demonstrated the procoagulant activity (PCA) of human adult liver progenitor cells (hALPCs) by thromboelastometry method on human blood and plasma. Clotting time (CT) of hALPCs was less than that of hepatocytes as evaluated in the thromboelastogram (in blood, 117.5±33.8 sec (n=15) vs. 285.8±87.0 sec (n=11), p<0.001) (in plasma, 112.6±18.4 sec (n=9) vs. 363.0±180.1 sec (n=5), p<0.05) (FIGS. 10A and 10B). The control CT, without addition of cells, was measured at 646.2±111.7 sec (n=15) in blood and at 781.9±150.5 (n=9) in plasma. A comparable PCA of hALPCs was observed when no extrinsic TF was added (FIG. 11). No PCA was obtained when the hALPCs culture medium, absence of cells, was placed in the thromboelastogram instead of cells (FIG. 12).

We also evaluated the PCA of hALPCs in the tubing loop model. Decrease of platelets count and increase of D-Dimers levels were observed after incubation of hALPCs with blood. Platelets from 295 000/µl to 109 000/µl (experiment 1) and from 310 000/µl to 134 to 000/µl (experiment 2); D-Dimers from 100 ng/ml to 700 ng/ml (experiment 2) and 95 ng/ml to 740 ng/ml (experiment 2).

Procoagulant Activity of Mesenchymal Cells

We also demonstrated the PCA of bone marrow mesenchymal stem cells (279.3±108.3 sec (n=3)), skin fibroblasts (121.8±26.53 sec (n=3)) and liver myofibroblasts (61.7±7.6 sec (n=3)) by thromboelastometry method on human whole blood. Bone marrow haematopoeitic stem cells were used as a control of non procoagulant cells (590.7±25.3 sec (n=3)) (FIG. 13).

Modulation of Procoagulant Activity of hALPCs

We first analyzed hALPCs PCA in coagulation factor deficient plasma. We showed that when using factor VII deficient plasma, co-factor of TF, the PCA hALPCs was only partially decreased (298.3±42.3 sec (n=3), p<0.01 as compared to PCA in normal plasma) (FIG. 14). We did not observe PCA of hALPCs in factor II (thrombin) or X deficient plasma, as for factor V deficient plasma but at a little level (FIG. 14). Furthermore and conversely to hepatocytes PCA (FIG. 15C), we showed that the hALPCs PCA was not fully inhibited by non fractionated heparin (225.8±149.8 sec (n=15)), low molecular weight heparin (112.3±22.5 sec (n=3)) or fondaparinux (209.7±149.7 sec (n=3)) (FIG. 15A), even if the dose was increased up to 5× (FIG. 23). No coagulation was observed when heparin was used in absence of cells.

Thrombin inhibitor drugs, hirudin or bivalirudin allowed only a partial control of hALPCs PCA (256.3±11.8 sec (n=3) and 380.8±114.7 sec (n=4), respectively) (FIG. 15B), even when increasing the dose (2× or 5×) (FIGS. 24 and 25). Hepatocytes PCA was controlled by thrombin inhibitor drugs, hirudin and bivalirudin (FIG. 15D). Control blood (in absence of cells) had a CT at 1075.0±107.2 with bivalirudin while no measurable coagulation was observed with hirudin.

Anti-vitamin K drugs (blood obtained from treated patients with INR 2 to 3) had no influence on thromboelastometry even for control (absence of cells) (data not shown).

Finally, we demonstrated that the concomitant use of bivalirudin with non fractionated heparin (1240.0±338.7 sec (n=3)) or enoxaparin (725.0±90.1 sec (n=3)) or fondaparinux (909.0±421.4 sec (n=3)) is a synergic combination, antithrombin activator and thrombin inhibitor, allowing to modulate the PCA of hALPCs (FIGS. 16A and B). No complete modulation of hALPCs PCA was obtained when combining heparin and enoxaparin or fondaparinux (FIG. 26).

Using analogous experiments, we demonstrated that non fractionated heparin can control PCA of bone marrow mesenchymal cells, skin fibroblasts but was inactive on liver myofibroblasts PCA (FIG. 27). The concomitant use of non fractionated heparin and bivalirudin was also shown to modulate the PCA of liver myofibroblasts, in contrast with bivalirudin alone (FIG. 28).

Analysis of the PCA of hALPCs hALPCs Express TF and TFPI

Figure 17:
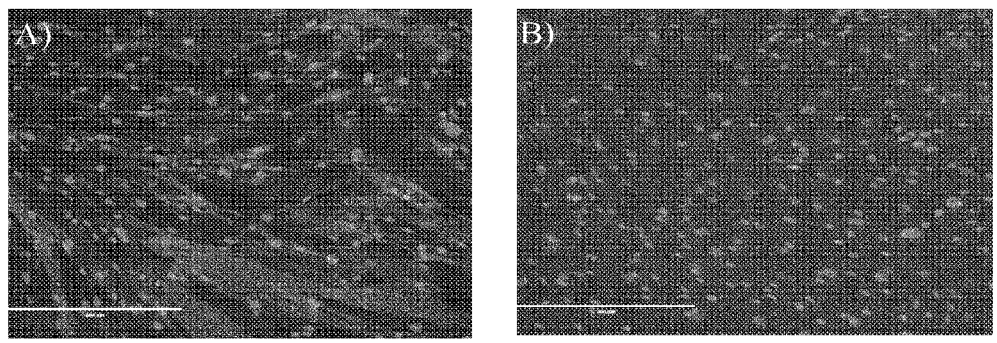

TF expression was first documented by immunofluorescence. As shown in FIG. 17, we found that all cells expressed TF constitutively (uniform cytoplasmic staining). Flow cytometry analysis of hALPCs confirmed a positive and specific staining for TF (94.9±1.0% for membrane bound form, 93.6±10.2% for cytosolic form as compared to control isotype 24.2±6.1% and 7.6±5.8% respectively and to unmarked cells 13.2±7.1% and 3.7±4.1% respectively; n=3).

We also assessed the expression of TF and its inhibitor TFPI at the mRNA level on using RT-PCR (FIG. 18). Both the membrane form and the alternatively-spliced variant of TF mRNA were expressed in hALPCs. TFPI was also expressed. In additional experiments, we used real-time RT-PCR to quantify TF, as-TF and TFPI mRNA levels. As shown in FIG. 19, the membrane TF variant was predominantly expressed (n=3). Furthermore, the expression of TF is more important for hALPCs compared to hepatocytes (n=3). On the contrary the expression of TFPI by hepatocytes was higher than that of hALPCs (n=3).

The role of TF in induction of PCA was determined by pre-incubation of cells with anti-human TF IgG. As shown in FIG. 20, PCA of hALPCs was only partially controlled by blocking TF (324.8±11.4 sec (n=5), p<0.01 as compared to absence of TF antibody) in contrast to hepatocytes, as previously demonstrated (Fisher et al., Transplantation. 2000; 69:303-307).

As already showed in FIG. 13, we only obtained a partial control of hALPCs PCA in factor VII deficient plasma confirming that the PCA of hALPCs was not completely related to TF.

hALPCs and Heparin

We observed only a small anti-Xa activity in plasma obtained after incubation of hALPCs (0.05±0.03 Ul/ml) and heparin at a concentration of 10 Ul/ml (FIG. 21), in correlation with the absence of anticoagulant effect of heparin alone on hALPCs.

Clinical Application-Specific Anticoagulation Protocol

The anticoagulation protocol was successfully applied as no thrombotic or hemorrhagic event occurred in both patients. As expected with bivalirudin use we observed a substantial increase in TT and limited in PT. Mild D-Dimers increase was noted in both patients, reaching 1480 ng/ml for the first patient and 1840 ng/ml for the second patient. Increase in PTT was observed in both patients, correlated with detectable anti-Xa activity (FIGS. 22A and B). No modification of portal flow by liver Doppler ultrasound was found during infusions in both patients.

What is claimed is:

1. A method for preventing thrombosis or thrombotic complications caused by in vivo transplantation of adult liver progenitor cells or for inhibiting procoagulant activity of said cells in vivo in a patient in need thereof, said method comprising administering to the patient
   (a) a liquid cell suspension via injection, the liquid cell suspension comprising:
      at least one antithrombin activator selected from the group consisting of heparin, unfractionated heparin and low molecular weight heparin; and
      the adult liver progenitor cells; and
   (b) an aqueous solution comprising at least one thrombin inhibitor selected from the group consisting of bivalirudin and hirudin,
   wherein (a), and (b) are administered to the patient simultaneously, separately or sequentially in any order.

2. The method of claim 1, wherein the adult liver progenitor cells are adult liver-derived progenitor or stem cells which express alpha-smooth muscle actin (ASMA) and albumin (ALB) and do not express cytokeratin-19 (CK-19), or are non-oval adult human liver-derived pluripotent progenitor cells which express hepatic cell markers and which are capable of differentiating into mature liver cells, insulin-producing cells, osteogenic cells and epithelial cells, or are non-oval adult human liver-derived pluripotent progenitor cells which express hepatic cell markers and which are capable of differentiating into mature liver cells, insulin-producing cells, osteogenic cells and endothelial cells.

3. The method of claim 1, wherein the cells are administered to the patient at a concentration of between $10^4$/ml to $10^8$/ml.

4. The method of claim 1, wherein the cells of the cell suspension
   are primary cells;
   are a cell line;
   have been subjected to storage and/or to proliferation or passaging;
   are induced to express one or more proteins; or
   are stably or transiently transformed with a nucleic acid.

5. The method of claim 1, wherein the antithrombin activator is unfractionated heparin, and wherein the unfractionated heparin is administered to the patient at a concentration of about 5-15 IU/ml.

6. The method of claim 1, wherein the thrombin inhibitor comprises bivalirudin and wherein the bivalirudin is administered to the patient during the administration of the cell suspension in an amount of 0.50-3.00 mg/kg body weight.

7. The method of claim 1, wherein the thrombin inhibitor comprises bivalirudin and wherein the bivalirudin is administered to the patient separate from the cell suspension of (a) in an amount of 0.2-0.6 mg/kg body weight, between consecutive administrations of the cell suspension.

8. The method of claim 1, wherein the thrombin inhibitor comprises bivalirudin and wherein the bivalirudin is administered to the patient separate from the cell suspension of (a) at 0.25 mg/kg body weight for 2 to 4 hours between consecutive administrations of the cell suspension.

9. The method of claim 1, wherein the thrombin inhibitor comprises hirudin and wherein the hirudin is administered to the patient in an amount of 0.2-0.6 mg/kg body weight.

10. The method of claim 1, wherein the antithrombin activator and the at least one thrombin inhibitor are administered simultaneously.

11. The method of claim 1, wherein the aqueous solution in (b) comprises one or more pharmaceutically acceptable excipients.

12. The method of claim 1, further comprising administering an immunosuppressive agent.

13. The method of claim 1, wherein the antithrombin activator is unfractionated heparin and the thrombin inhibitor comprises bivalirudin.

* * * * *